(12) United States Patent
Schermers et al.

(10) Patent No.: US 11,166,782 B1
(45) Date of Patent: Nov. 9, 2021

(54) IMPLANTABLE MARKER AND A METHOD OF IMPLANTING MARKERS

(71) Applicant: SIRIUS MEDICAL SYSTEMS B.V., Eindhoven (NL)

(72) Inventors: Bram Schermers, Eindhoven (NL); Adrianus Cornelis Petrus Van Leijsen, Eindhoven (NL); Hubert Cecile Francois Martens, Eindhoven (NL)

(73) Assignee: SIRIUS MEDICAL SYSTEMS B.V.

( * ) Notice: Subject to any disclaimer, the term of this patent is extended or adjusted under 35 U.S.C. 154(b) by 0 days.

(21) Appl. No.: 17/022,019

(22) Filed: Sep. 15, 2020

Related U.S. Application Data

(63) Continuation of application No. PCT/IB2020/056785, filed on Jul. 19, 2020.

(51) Int. Cl.
*A61B 5/05* (2021.01)
*A61B 5/06* (2006.01)
(Continued)

(52) U.S. Cl.
CPC ............ *A61B 90/39* (2016.02); *A61B 5/062* (2013.01); *H01F 7/0205* (2013.01);
(Continued)

(58) Field of Classification Search
CPC ........... A61B 90/39; A61B 5/05; A61B 5/062; A61B 2090/3957; A61B 2090/3987
See application file for complete search history.

(56) References Cited

U.S. PATENT DOCUMENTS

| 8,244,377 B1 | 8/2012 | Pianca et al. |
| 10,595,957 B2 | 3/2020 | Mayes et al. |

(Continued)

FOREIGN PATENT DOCUMENTS

| EP | 0961301 A1 | 12/1999 |
| EP | 1341466 B1 | 9/2009 |

(Continued)

*Primary Examiner* — Patricia J Park
(74) *Attorney, Agent, or Firm* — The Roy Gross Law Firm, LLC; Roy Gross

(57) ABSTRACT

Implantable magnetic markers (seeds) provide a higher degree of flexibility and convenience. The magnetic field that a marker provides is determined by the magnetic properties of the materials used and the dimensions of the marker—in general, a larger marker is easier to locate. Larger diameter markers may be used, but they should be much smaller than the average tumor size if they are to provide a useful degree of localization.

An implantable magnetic marker is provided with two or more magnetic elements comprising permanent magnets connected by a mechanical connector to resiliently retain a first orientation when deployed and a second orientation before and/or during implantation. This allows complex magnetic configurations to be implanted, while retaining a simplified implantation method independent of the number of magnetic elements used. The transverse extent of the magnetic marker may be significantly reduced for implantation, allowing smaller needle diameters (smaller needle gauges) to be used or a larger number of smaller marker elements. This also allows significantly less longitudinal extents to be used.

In addition, the two or more magnetic elements may be aligned to increase the transverse extent by increasing the transverse extent after implantation. This may increase detectability.

29 Claims, 13 Drawing Sheets

(51) Int. Cl.
*A61B 90/00* (2016.01)
*A61B 17/00* (2006.01)
*H01F 7/02* (2006.01)

(52) U.S. Cl.
CPC ............... *A61B 2090/3954* (2016.02); *A61B 2090/3987* (2016.02); *A61B 2503/40* (2013.01)

(56) References Cited

U.S. PATENT DOCUMENTS

| | | |
|---|---|---|
| 2006/0020317 A1 | 1/2006 | Flach et al. |
| 2008/0039676 A1* | 2/2008 | Fischell ............ A61M 37/0069 600/12 |
| 2013/0253550 A1* | 9/2013 | Beisel ................ A61B 17/1114 606/153 |
| 2014/0336696 A1* | 11/2014 | Kugler ............. A61B 17/12009 606/201 |
| 2016/0354178 A1* | 12/2016 | Mayes .................... A61B 5/05 |
| 2017/0119394 A1* | 5/2017 | McWeeney ............ A61B 17/11 |
| 2019/0223975 A1* | 7/2019 | Agostinelli ............ A61B 5/062 |

FOREIGN PATENT DOCUMENTS

| | | |
|---|---|---|
| WO | 2001008578 A1 | 2/2001 |
| WO | 2014013235 A1 | 1/2014 |
| WO | 2016068700 A1 | 5/2016 |

\* cited by examiner

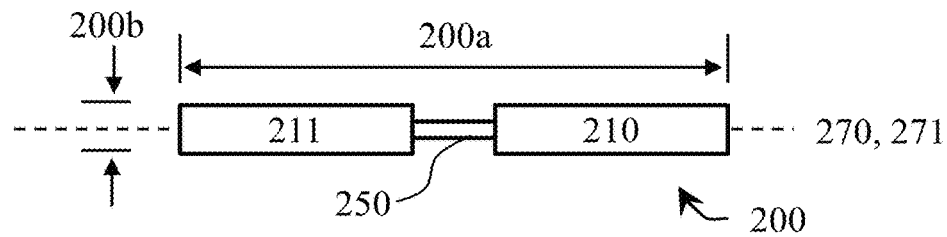
Fig. 2A
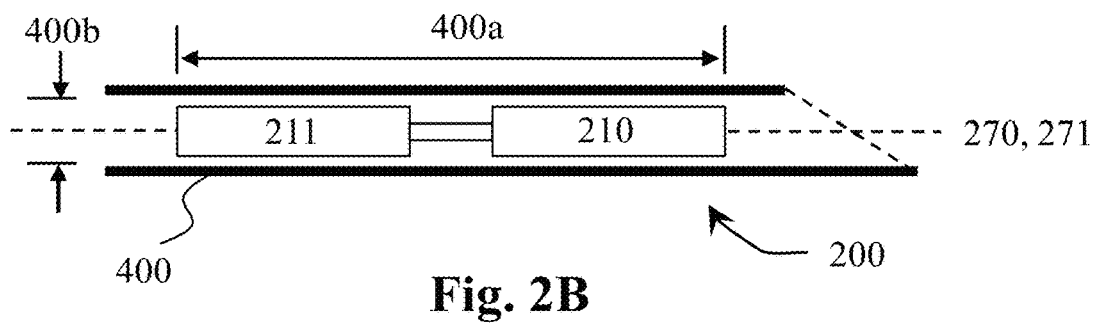
Fig. 2B
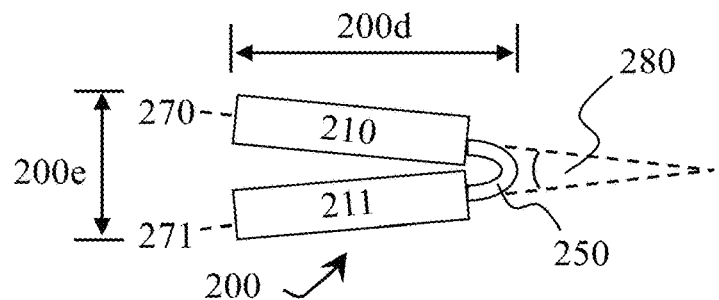
Fig. 2C(i)
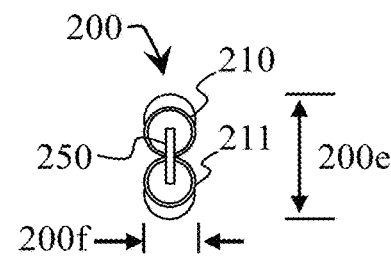
Fig. 2C(ii)
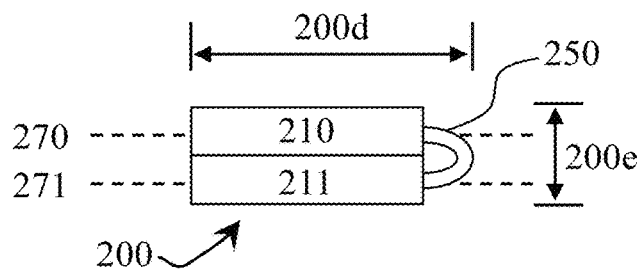
Fig. 2D(i)
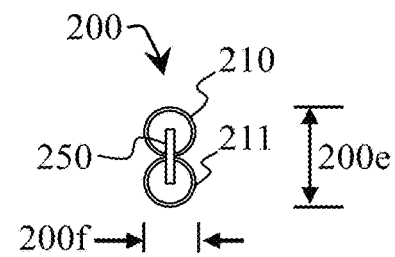
Fig. 2D(ii)

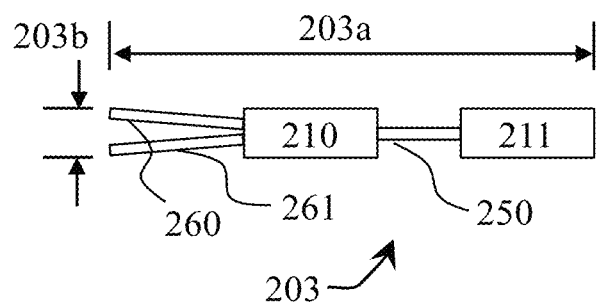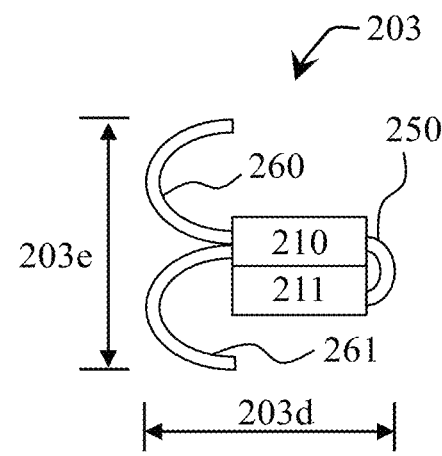
Fig. 8A                Fig. 8B
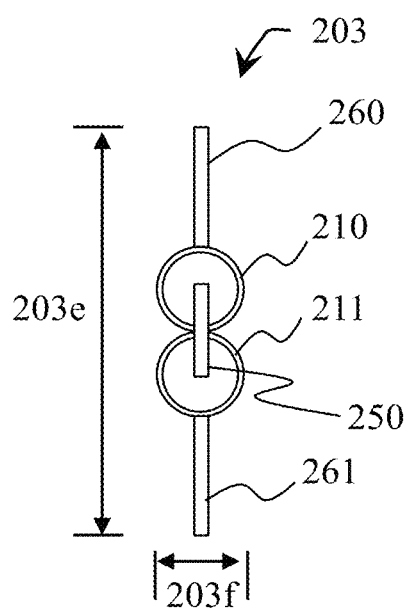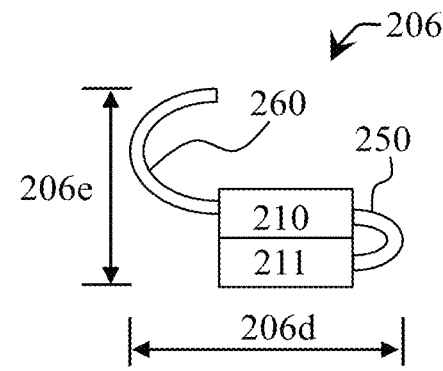
Fig. 8C                Fig. 8D

IMPLANTABLE MARKER AND A METHOD OF IMPLANTING MARKERS

CROSS REFERENCE TO RELATED APPLICATIONS

This application is a Track One Continuation of PCT Patent Application No. PCT/IB2020/056785 having International filing date of Jul. 19, 2020. The content of the above application is incorporated by reference as if fully set forth herein in its entirety.

FIELD OF THE INVENTION

The present disclosure relates to an implantable marker, a kit comprising one or more implantable markers and a detection unit, and a method of implanting an implantable marker.

BACKGROUND OF THE INVENTION

During both invasive and non-invasive treatments and therapies, it is important that health professionals are able to accurately locate areas of interest. Frequently, professionals rely on sight and manual manipulation to find and remember areas of interest, often marking an outer surface of skin. In practice, imaging equipment such as X-ray and/or ultrasound, may also be used to assist in the location—however, this relies on being able to distinguish the area of interest from the surrounding tissue using the imaging technologies.

Implantable magnetic markers (seeds) are also available. These provide a higher degree of flexibility and convenience, but still require considerable effort by the healthcare professional to detect the disposition (localization) of the marker. The magnetic field that a marker provides is determined by the magnetic properties of the materials used and the dimensions of the marker—in general, a larger marker is easier to locate. Larger diameter markers may be used, but they should be much smaller than the average tumor size if they are to provide a useful degree of localization.

It is an object of the invention to provide an increase in magnetic field strength of the markers without substantially reducing the tissues and therapies that they can be used for.

GENERAL STATEMENTS

According to a first aspect of the current disclosure, there is provided an implantable magnetic marker for providing a detectable magnetic field, the marker comprising: a first magnetic element comprising a permanent magnet with a first north pole and a first south pole; a second magnetic element comprising a permanent magnet with a second north pole and a second south pole; a mechanical connector, extending between the first and second magnetic elements, the mechanical connector being configured and arranged: to resiliently retain a first orientation between the first magnetic element and the second magnetic element when disposed in human or animal tissue, wherein the magnetic marker is bounded by an implanted marker volume with a longitudinal implanted extent and a transverse implanted extent; and to assume a second orientation between the first magnetic element and the second magnetic element before and/or during implantation, wherein the magnetic marker is bounded by an implantation volume with a longitudinal implantation extent and a transverse implantation extent, whereby: the transverse implanted extent is significantly greater than the transverse implantation extent; and the longitudinal implanted extent is significantly less than longitudinal implantation extent.

By using two or more magnetic elements comprising permanent magnets, connected by a mechanical connector, different orientation angles between the two or more magnetic elements may be used after implantation, when the marker is disposed in human or animal, compared to during (and/or before) implantation. Complex magnetic configurations may be implanted, while retaining a simplified implantation method independent of the number of magnetic elements used. This allows the extent of the magnetic marker to be reduced for implantation, allowing smaller needle diameters (smaller needle gauges) to be used or a larger number of smaller marker elements. The marker may be configured and arranged to provide one or more predetermined second orientation angles, using the attractive and repulsive magnetic forces to assist in deployment, anchoring and/or increasing the energy of a detectable signal.

The use of permanent magnets rather than soft magnetic materials allows detection without requiring regions of tissue to be exposed to high levels of energy. In addition, such systems that require the soft magnets to be energized create a relatively high level of signal noise against which the magnetic response is to be detected—in contrast, detection of permanent magnets generally only needs to distinguish against low levels of environmental background magnetism, and may be more accurate.

Additionally, the two or more magnetic elements may be aligned to reduce the longitudinal extent by increasing the transverse extent after implantation. This may increase detectability.

According to a further aspect of the current disclosure, there is provided an implantable magnetic marker, wherein the first and/or second permanent magnetic elements comprise: an enclosure with a cavity, enclosing the permanent magnet in said cavity.

By providing an enclosure enclosing at least one permanent magnet, properties of the permanent magnet, such as size, shape, materials, finishing, may be optimized separately to a high degree from the properties of the magnetic element.

For example, the enclosure may be configured and arranged to substantially hermetically seal the permanent magnet in its cavity. As it is the outer surfaces of the enclosure which are exposed to tissue, the enclosure may be configured and arranged to comprise materials with a higher degree of corrosion resistance and/or biocompatibility. In contrast, the permanent magnet may be optimized for magnetic field strength without requiring a high-degree of biocompatibility.

According to another aspect of the current disclosure, the magnetic element enclosure may be configured and arranged to allow the disposition of the north pole and/or south pole in said cavity to change during use.

Use of enclosure allows the magnetic pole disposition to be configured and arranged to be the same, similar or different to the physical disposition of the magnetic element, allowing displacement and/or rotation. In such an embodiment, it may be advantageous to use weakly magnetic materials in the enclosure with a reduced, a low or an insignificant degree of ferromagnetism when exposed to the field strengths produced by the permanent magnets used.

According to yet another aspect of the current disclosure, the mechanical connector is attached to an outer surface of the enclosure comprised in the first and/or second magnetic element.

One or more attachments to the enclosure may be advantageous when using permanent magnet materials to which attachment (for example, by gluing) may not be secure enough for reliable, regulated use, and welding is not feasible or desired.

According to a still further aspect of the current disclosure, the mechanical connector extends between ends of the first and second magnetic elements having the same pole or having the opposite pole. The same pole may be retained at a predetermined and/or controlled close proximity. Opposite poles may be retained with a predetermined and/or controlled separation.

This may increase the outward magnetic field generated by the marker, and hence may increase detectability of the magnetic marker.

According to another aspect of the current disclosure, the implantable magnetic marker further comprises one or more mechanical anchors, configured and arranged to resist changes in position of one or more magnetic elements when disposed in human or animal tissue.

One or more mechanical anchors may be configured and arranged as tissue anchors to assist in fixation of the magnetic marker upon implantation and/or resist migration of the magnetic marker after implantation. It may be advantageous to resist movement and/or migration due to magnetic attraction and/or repulsion between proximate magnetic markers, proximate magnetic elements, a magnetic marker and any implantation channel, a magnetic marker and any surgical instrument used before, during or after implantation, or any combination thereof.

Optionally, the one or more mechanical anchors may be configured and arranged to be substantially retracted before and/or during implantation, and to be transversely extended after implantation.

Optionally, the one or more mechanical anchors may be configured and arranged to be transversely extended during implantation.

By exerting a force against an inner surface of the bore during implantation, the resistance against movement of the magnetic marker may be significantly increased. This may be advantageous in preventing unwanted deployment of the implantable magnetic marker during implantation.

According to yet another aspect of the current disclosure, a magnetic marker is provided further comprising: a further magnetic element comprising a permanent magnet with a further north pole and a further south pole; a further mechanical connector, extending between the further magnetic element and the second magnetic element, the further mechanical connector being configured and arranged: to resiliently retain a further first orientation between the further magnetic element and the second magnetic element when disposed in human or animal tissue; and to assume a further second orientation between the further magnetic element and the second magnetic element.

Advantageously, a plurality of magnetic element may be implanted in controlled configurations. In some configurations, this is further increasing the combined magnetic field strength available for detection.

Optionally, the first and further magnetic elements may have a longitudinal extent substantially less than the longitudinal extent of the second magnetic element.

In embodiments where the magnetic marker comprises three or more magnetic elements, the mechanical connectors may be configured to allow the two outer magnetic elements to fold towards a central magnetic element. This may allow the overall longitudinal implanted extent of the magnetic marker to be reduced with a smaller increase in the largest transverse implanted extent.

Optionally, the ends of the further magnetic element and the first magnetic element having opposite poles may be retained at a predetermined and/or controlled close proximity.

This may provide a smaller increase in the largest transverse implanted extent. In addition, the use of the attraction due to the opposite poles of the reduced extent magnetic elements may reduce the risk of incorrect or insufficient deployment.

According to a still further aspect of the current disclosure, a kit of parts is provided for locating a tissue area of interest comprising: one or more implantable markers including one or more permanent magnets; and a magnetic marker field probe having one or more magnetic sensors, configured and arranged to measure a magnetic field generated by the one or more permanent magnets after being disposed in human or animal tissue.

According to a further aspect of the current disclosure, a kit of parts is provided for implanting a magnetic marker, comprising: one or more implantable markers, being bounded by one or more marker implantation volumes and including one or more permanent magnets; and an implantation channel having a bore substantially equal to or greater than the one or more marker implantation volumes.

Optionally, the implantation channel may comprise one or more weakly magnetic materials.

According to another aspect of the current disclosure, a method is provided for implanting an implantable magnetic marker, the magnetic marker comprising: a first magnetic element comprising a permanent magnet with a first north pole and a first south pole; a second magnetic element comprising a permanent magnet with a second north pole and a second south pole; a mechanical connector, extending between the first and second magnetic elements, the method comprising: after implantation, resiliently retaining a first orientation between the first magnetic element and the second magnetic element when disposed in human or animal tissue, wherein the magnetic marker is bounded by an implanted marker volume with a longitudinal implanted extent and a transverse implanted extent; and before or during implantation, assuming a second orientation between the first magnetic element and the second magnetic element wherein the magnetic marker is bounded by an implantation volume with a longitudinal implantation extent and a transverse implantation extent, whereby: the transverse implanted extent is significantly greater than the transverse implantation extent; and the longitudinal implanted extent is significantly less than longitudinal implantation extent.

According to another aspect of the current disclosure, a method is provided further comprising: during implantation, moving the magnetic marker through an implantation channel, the implantation channel having a transverse bore dimension substantially equal to or greater than the transverse implantation extent of the magnetic marker.

Additionally or alternatively, the implantation channel may have a longitudinal bore dimension substantially equal to or greater than the longitudinal implantation extent of the magnetic marker.

Additionally or alternatively, the implantation channel may have bore dimensions substantially equal to or greater than the implantation volume of the magnetic marker.

This means that the degree of resistance to movement of the marker through the bore may be predetermined and/or controlled.

According to yet another aspect of the current disclosure, a method is provided comprising: during and/or after implantation, retaining the north pole of the first magnetic element and the north pole or south pole of the second magnetic element in proximity, in close proximity, in very close proximity, in contact, or any combination thereof.

Additionally or alternatively, a method is provided comprising: during and/or after implantation, retaining the south pole of the first magnetic element and the north pole or south pole of the second magnetic element in proximity, in close proximity, in very close proximity, in contact, or any combination thereof.

This may increase the outward magnetic field generated by the marker, and hence may increase detectability of the magnetic marker.

According to still yet another aspect of the current disclosure, a method is provided comprising: during and/or after implantation, folding the first magnetic element towards the second magnetic element and/or folding the second magnetic element towards the first magnetic element, whereby the longitudinal implanted extent is reduced compared to the longitudinal implantation extent.

Additionally or alternatively, a method is provided comprising: during and/or after implantation, folding the first magnetic element towards the second magnetic element and/or folding the second magnetic element towards the first magnetic element, whereby the transverse implanted extent is increased compared to the transverse implantation extent.

The mechanical connectors may be configured to allow two magnetic elements to fold towards each other. This may allow the overall longitudinal implanted extent of the magnetic marker to be reduced.

Alternatively, the magnetic marker may further comprises: a further magnetic element comprising a permanent magnet with a further north pole and a further south pole; a further mechanical connector, extending between the further magnetic element and the second magnetic element, the further mechanical connector being configured and arranged: to resiliently retain a further first orientation between the further magnetic element and the second magnetic element when disposed in human or animal tissue; and to assume a further second orientation between the further magnetic element and the second magnetic element before and/or during implantation; the method further comprising: during and/or after implantation, folding the first magnetic element towards the second magnetic element and/or folding the second magnetic element towards the first magnetic element; and during and/or after implantation, folding the further magnetic element towards the second magnetic element and/or folding the second magnetic element towards the further magnetic element; whereby the longitudinal implanted extent is reduced compared to the longitudinal implantation extent.

Additionally or alternatively, the transverse implanted extent may be increased compared to the transverse implantation extent.

In embodiments where the magnetic marker comprises three or more magnetic elements, the mechanical connectors may be configured to allow the two outer magnetic elements to fold towards a central magnetic element. This may allow the overall longitudinal implanted extent of the magnetic marker to be reduced with a smaller increase in the largest transverse implanted extent According to still further aspect of the current disclosure, a method is provided wherein the implantable magnetic marker further comprises one or more mechanical anchors, and the method further comprises: during and/or after implantation, allowing the one or more mechanical anchors to adopt a first shape and/or a first orientation to the magnetic marker whereby changes in position of one or more magnetic elements are significantly resisted in human or animal tissue.

Optionally, the method may further comprise: during implantation, allowing the one or more mechanical anchors to adopt a second shape and/or a second orientation to the magnetic marker whereby a force is exerted against an inner surface of the implantation channel to provide a significant degree of resistance against movement of the magnetic marker through the implantation channel.

This may be advantageous in preventing unwanted deployment of the implantable magnetic marker during implantation.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments and which are not necessarily drawn to scale, wherein:

FIGS. 2A, 2C(i), 2C(ii), 2D(i) and 2D(ii) depict plan views of a first embodiment of an implantable magnetic marker in different orientations before, during and after implantation;

FIG. 2B depicts a longitudinal cross-section of the first embodiment of an implantable magnetic marker in an implantation channel;

FIGS. 8A, 8B, 8C and 8D depict plan views of further embodiment of an implantable magnetic marker comprising one or more mechanical (tissue) anchors;

DETAILED DESCRIPTION OF THE INVENTION

In the following detailed description, numerous non-limiting specific details are given to assist in understanding this disclosure. It will be obvious to a person skilled in the art that the computer processing part of the method may be implemented on any type of standalone system or client-server compatible system containing any type of client, network, server, and database elements.

Figure 1:
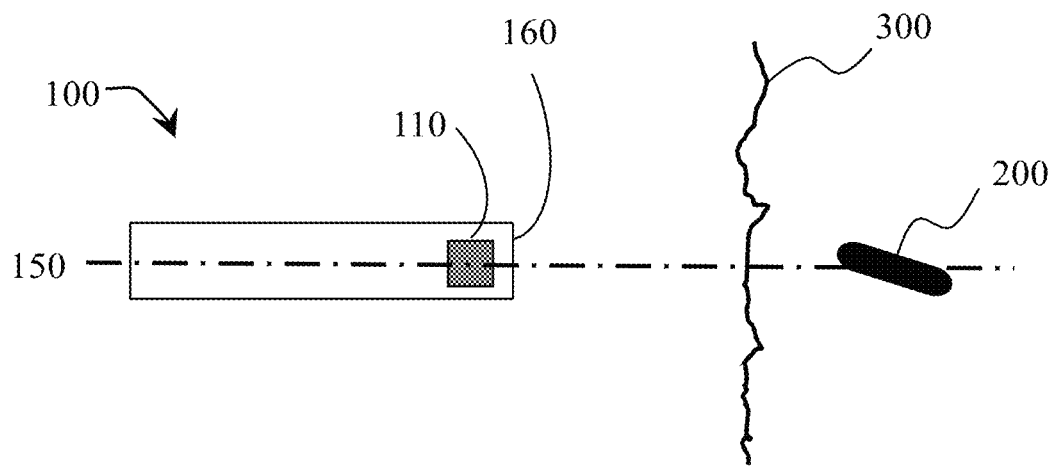
FIG. 1 depicts a longitudinal cross-section through a magnetic field probe for detecting a magnetic marker according to the invention.

FIG. 1 depicts a longitudinal cross-section through a magnetic marker field probe 100 for detecting a disposition (localization) of an implantable marker 200 according to the invention. As depicted, the magnetic marker 200 is implanted below an outer surface of skin 300 to mark an area of interest—this may be a few millimeters or a few centimeters below the outer surface of the skin. This may also be called depth. The marker 200 is configured to generate, in use, a magnetic field—it may comprise, for example, a magnetic dipole.

The marker 200 may be implanted in any convenient way, such as by injection. The injection may be, for example, into soft tissue or organs, or delivery via a bronchoscope to lung bronchi, or coloscope to colon. The method of implantation may depend on, for example, the depth required, the subsequent procedure to be performed, the size of the area of interest, the location of the area of interest, the type of tissue in the area, and the type of tissue surrounding the area. It may be implanted immediately before detection, or some time earlier.

The probe 100 comprises one or more magnetic sensors 110, typically proximate the distal end 160 of the probe 100. The one or more magnetic sensors 110 are configured to measure at least the vector of the local magnetic field (Bx, By, Bz)—this may include a background measurement and the field generated by the marker 200 when the probe 100 is in close proximity. The magnetic field probe may extend along a probe longitudinal axis 150.

The one or more magnetic sensors 110 may be any suitable type, such as magnetometers, flux gate sensors, geomagnetic sensors, Lorentz force digital MEMS, magneto-inductive sensors, magneto-resistive sensors, Hall sensors, magnetic tunnel junctions and any combination thereof. Many IC packages are available which are small and contain 3 axis detection. So a 'many-axis' solution may be provided with simple PCB design and preferably a smaller probe diameter.

The distal end 160 may be configured and arranged to be disposed close to an outer surface of skin 300. Additionally, or alternatively, the distal end 160 may be configured and arranged to:
- contact an outer surface of skin 300;
- be inserted through an outer surface of skin 300;
- be inserted into a body cavity through a natural orifice;
- be inserted into a body cavity through a surgical incision or wound; or
- any combination thereof.

The distal end 160 may be disposed at a distance from the outer surface of skin 300—a spacer may be used to maintain a fixed distance, or the distance may be zero if the probe 100 is further configured and arranged to contact the outer surface of skin 300. The probe 100 may be further configured and arranged to be pushed against the outer surface of skin 300 to create an indent which may further reduce the distance between the distal end 160 of the probe 100 and the marker 200. In general, the smaller the distance between the probe 100 and the marker, the greater the amplitude of any signal measured. For some treatments, the probe 100 may further configured and arranged to be inserted through the outer surface of skin 300 and/or into a body cavity to further reduce the distance between probe 100 and marker 200. This may be, for example, via a surgical incision or via a natural orifice.

The magnetic field probe 100 may also be configured and arranged to detect a disposition (localization) of one or more implantable magnetic element. Typically, such conventional elements comprise a magnetic dipole, and are approximately cylindrical with:
- a diameter of 1.45 mm, a length of 2.19 mm and a remnant field (Br) of 1.43 T (Neodymium N52), or
- a diameter of 1.75 mm, a length of 5 mm and a remnant field (Br) of 1.43 T (Neodymium N52); or
- a diameter of 1.45 mm and a length of 4.7 mm (also Neodymium N52).

These examples may be implanted using a 1.8 mm inner diameter (bore)/2.1 mm outer diameter 14G needle.

The detectability of a magnetic element depends on parameters such as the volume of the magnetic material and the magnetic material properties. For example, higher grades of neodymium may increase detectability, but these may be more costly.

The inventors have considered how greater volumes of magnetic material could be used. One of the insights upon which the invention is based is that using larger magnetic elements and/or a plurality of magnetic elements may be disadvantageous:
- longer markers may be used, but they should be preferably much shorter than the average tumor size if they are to provide a useful degree of localization
- larger diameter markers may require a larger needle gauge to be used for implantation, which limits the types of tissues and therapies they can be used for. For example, not all tumors are suitable to receive a large gauge needle
- a plurality of magnetic elements may be implanted together. However, the attraction of opposite poles and repulsion of the same poles means that they will tend to align to each other in a generally unpredictable way. In many cases, such a plurality of magnetic elements may naturally and/or physically align in a way that reduces the outward magnetic field lines—this may be detrimental to detectability.

Markers comprising more than one joined element are known from U.S. Pat. No. 10,595,957, disclosing markers comprising a plurality of magnetically soft elements. U.S. Pat. No. 10,595,957 considers an ideal magnetic marker to be one that becomes magnetized in the presence of a magnetic field and exhibits no permanent magnetic remanence (retained magnetization) when the field is removed, or in other words, an ideal marker is magnetically soft, i.e. formed from magnetically soft material or behaving as if it is magnetically soft. The induced field in the material (magnetization) is detected by the probe. The multiple facets also provide superior ultrasound response. U.S. Pat. No. 10,595,957 considers permanent magnets as generally unsuitable for joining because they can attract or be attracted by other ferromagnetic objects, and typically have very low magnetic susceptibility.

In practice, the magnetic markers in this disclosure have a complex 3D-volume, which may vary significantly before implantation, during implantation and/or after implantation. Optimization in more than one degree of freedom may be required to achieve satisfactory deployment of the desired magnetic configuration.

However, to explain the principles behind the embodiments, the figures in this disclosure mainly illustrate 2D examples which appear have cross-sections which are substantially symmetrical about central longitudinal planes.

The inventors have realized that it is highly advantageous to use implantable magnetic markers comprising two or more permanent magnetic elements, coupled together with one or more mechanical connectors. Such a magnetic marker 200 is depicted schematically in FIGS. 2A, 2B, 2C(i), 2C(ii), 2D(i) and 2D(ii). More specifically, FIG. 2C(i), 2C(ii), FIG. 2D(i) and FIG. 2D(ii) depict schematic plan views of the magnetic marker 200 after implantation.

FIG. 2A depicts a schematic plan view of the magnetic marker 200 before implantation. The magnetic marker 200 comprises:
- a first 210 magnetic element, and comprising a permanent magnet. The permanent magnet has a first north pole and a first south pole (not depicted in FIG. 2);
- a second 211 magnetic element, and comprising a permanent magnet. The permanent magnet has a second north pole and a second south pole (not depicted in FIG. 2); and
- a mechanical connector 250, extending between the first 210 and second 211 magnetic elements.

Before implantation, the magnetic marker 200 has a marker volume with a longitudinal extent 200a, a first transverse extent 200b and a second transverse extent (not depicted). The extents 200a, 200b are determined by the outer edges of all magnetic elements 210, 211, all mechanical connectors 250 and the orientation between the first magnetic element 210 and the second magnetic element 211. The transverse extents 200b may vary at different positions along the longitudinal extent 200a. The longitudinal extent 200a may vary at different positions along the transverse extent 200b.

FIG. 2B depicts a longitudinal cross-section through the marker 200, and through an implantation channel 400 having a suitable bore with a longitudinal bore extent 400a, a first transverse bore extent 400b and a second transverse bore extent (not depicted). The sharpened point on the right-hand side of the implantation channel 400 is an aperture from which the magnetic elements will emerge in the order first magnetic element 210, mechanical connector 250, then second magnetic element 211.

The implantation channel 400 may be comprised in an implantation tool.

To be able to pass easily through the bore 400b, the volume boundaries of the magnetic marker 200 are preferably an implantation volume substantially equal to or smaller than the bore dimensions 400a, 400b of the implantation channel 400. During implantation, the boundaries (usually the walls of the channel 400) of the implantation channel 400 limit the maximum marker implantation volume, otherwise the magnetic marker 200 may not move easily through the channel. Depending on the configuration and arrangement, the magnetic marker 200 may exert a force on the boundaries which may influence the resistance to movement through the implantation bore 400b.

the maximum marker implantation volume is thus considered to have a longitudinal implantation extent substantially equal to the longitudinal bore extent 400a, a first transverse extent substantially equal to the first transverse bore extent 400b, and a second transverse extent substantially equal to the second transverse bore extent (not depicted). Alternatively or additionally, the longitudinal bore extent 400a may be greater than the longitudinal marker implantation extent 200a. Alternatively or additionally, a first transverse bore extent 400b may be greater than the first transverse marker implantation extent 200b. Alternatively or additionally, a second transverse bore extent may be greater than the second transverse marker implantation extent.

Any shape of bore may be considered—a spherical implantation volume may be considered, with a diameter equal to the largest of a longitudinal implantation extent 400a, a first transverse implantation extent 400b or a second transverse implantation extent. Similarly, a rectangular tank implantation volume may be considered, with a height equal to a first transverse implantation extent 400b, a width equal to a second transverse implantation extent (not depicted) and a length equal to a longitudinal implantation extent 400a. Similarly, a capsule implantation volume may be considered, with a diameter equal to a transverse implantation extent 400b and a length equal to a longitudinal implantation extent 400a (or equal to a longitudinal implantation extent 400a minus (−) a transverse extent 400b). Similarly, an ellipsoid implantation volume or a conical frustum implantation volume may be used.

It is particularly advantageous to consider a substantially cylindrical bore 400b, such as a hollow injection needle. A cylindrical implantation volume may then be considered with a length equal to a longitudinal implantation extent 400a, and an inner diameter equal to the larger of a first transverse implantation extent 400b and a second transverse implantation extent (not depicted).

FIG. 2C(i) and FIG. 2C(ii) depict schematic plan views of the magnetic marker 200 after implantation, wherein the mechanical connector 250 resiliently retains an orientation between the first magnetic element 210 and the second magnetic element 211 with a first orientation difference. The difference in orientation may be in any direction—in practice, the first magnetic element 210 and second magnetic element 211 may be disposed along skewed longitudinal axes which do not necessarily intersect.

As depicted in FIG. 2C(i), the first magnetic element 210 is disposed along a first central longitudinal plane 270, and the second magnetic element 211 is disposed along a second central longitudinal plane 271. The first central longitudinal plane 270 and the second central longitudinal plane 271 intersect at an angle 280 on the side of the mechanical connector 250.

In other words, after implantation, the first magnetic element 210 is folded back towards the second magnetic element 211 to form an approximately V-shaped magnetic marker 200 when viewed along the first 270 and second 271 central longitudinal planes. In FIG. 2C(i), the longitudinal direction of the marker 200 is depicted horizontally and a first transverse direction is depicted vertically. The marker 200 has an implanted marker volume with:
- a maximum longitudinal extent 200d from the end of the magnetic elements 210, 211 to the outer edge of the mechanical connector 250; and
- a maximum first transverse extent 200e between the outer edges of the magnetic elements 210, 211 at the end with the largest transverse separation.

FIG. 2C(ii) depicts an end view from the side of the mechanical connector 250. The first transverse direction is depicted vertically, and a second transverse direction is depicted horizontally. The marker 200 implanted volume further has:
- a maximum second transverse extent 200f, between the outer edges of the magnetic elements 210, 211. In this example, it is approximately a transverse extent of the first 210 or second 211 magnetic element.

So, in summary, the magnetic marker 200 may be considered to be bounded by an implanted marker volume with a longitudinal implanted extent 200*d*, a first transverse implanted extent 200*e*, and a second transverse implanted extent 200*f*.

By disposing the first 210 and second 211 magnetic elements at an orientation 280 to each other after deployment, the transverse implanted extent 200*ef* becomes significantly greater than the transverse implantation extent 400*b*; and the longitudinal implanted extent 200*d* is significantly less than longitudinal implantation extent 400*a*.

In the terms of this disclosure, the following are considered significant:

an increase in a transverse implanted extent 200*ef* of at least 0.1× a transverse extent of a magnetic element 210, 211. Increases of 0.125, 0.25, 0.5, 0.75 and 1, 2×, 3× and 4× are considered increasingly significant; and a decrease in a longitudinal implanted extent 200*d* of at least 0.1× a transverse extent of a magnetic element 210, 211. Decreases of 0.125, 0.25, 0.5, 0.75, 1×, 2×, 3× and 4× are considered increasingly significant.

This may increase the volume of magnetic material present by providing a plurality of smaller permanent magnetic elements 210, 211 in predetermined and/or controlled orientations and/or proximities to each other. In other words, the plurality of magnetic elements 210, 211 may be aligned to reduce the implanted longitudinal extent 200*d* by increasing one or more implanted transverse extents 200*ef*. By using two or more magnetic elements 210, 211 in proximity, a field strength, similar to a larger dimensioned permanent magnet. may be provided using a plurality of smaller dimensioned permanent magnets 210, 211. In general, smaller dimensioned magnetic elements 210, 211 are easier to implant. as they may use a smaller bore of implantation channel 400.

In addition, the use of permanent magnets rather than soft magnetic materials allows detection without requiring regions of tissue to be exposed to high levels of energy. In addition, such systems that require the soft magnets to be energized create a relatively high level of signal noise against which the magnetic response is to be detected—in contrast, detection of permanent magnets generally only needs to distinguish against low levels of environmental background magnetism, and may be more accurate.

Any shape of implanted volume may be considered—a spherical implanted volume may be considered, with a diameter equal to the largest of the longitudinal implanted extent 200*d*, a first transverse implanted extent 200*e* or a second transverse implanted extent 200*f*. Similarly, a rectangular tank implanted volume may be considered, with a height equal to a first transverse implanted extent 200*e*, a width equal to a second transverse implanted extent 200*f* and a length equal to a longitudinal implanted extent 200*d*. Similarly, a capsule implanted volume may be considered, with a diameter equal to a first or second transverse implanted extent 200*ef*, and a length equal to a longitudinal implanted extent 200*d* (or equal to a longitudinal implanted extent 200*d* minus (−) a first or second transverse implanted extent 200*ef*). Similarly, an ellipsoid implanted volume or a conical frustrum implanted volume may be used.

It is particularly advantageous to consider a cylindrical implanted volume with a length equal to a longitudinal implanted extent 200*d* and diameter equal to the largest of a first transverse implanted extent 200*e* and a second transverse implanted extent 200*f*.

It may be advantageous to use the similar or identical volume definitions for implantation and implanted volumes.

An example of a different implanted orientation 280 is depicted in FIG. 2D(i) and (i). These figures are the same as FIGS. 2C(i) and 2C(ii) except for:

the first longitudinal plane 270 and the second longitudinal plane 271 are substantially parallel, instead of intersecting at an orientation angle 280;

the first transverse extent 200*e* between the outer edges of the magnetic elements 210, 211 is substantially the same at both ends of the magnetic elements 210, 211

In some configurations, this may provide the most compact arrangement of the magnetic elements 210, 211, greatly reducing the first transverse extent 200*e*.

For example, the magnetic marker 200 may be configured and arranged under ideal circumstances to fully deploy as depicted in FIG. 2D(i) and (ii). However, it is possible that in practice, when disposed in human or animal tissue, the magnetic elements 210, 211 may not fully come into contact at both ends, resulting in the angular separation depicted in FIG. 2C(i) and (ii), where one end of the magnetic elements 210, 211 are closer to each other than the other end.

Alternatively, the magnetic marker 200 may be configured and arranged under ideal circumstances to fully deploy as depicted in FIG. 2C(i) and (ii)—for example, such a V shape may provide more resistance against movement within tissue in one direction compared to another.

For example, it may be advantageous for the first longitudinal plane 270 and the second longitudinal plane 271 to intersect at an orientation angle 280 in the range 0 degrees to 50 degrees. Smaller orientation angles 280 may provide a more compact configuration of the magnetic elements 210, 211. Orientation angles 280 close to 0 degrees may be considered substantially equivalent to the longitudinal planes 270, 271 being parallel as depicted in FIG. 2D (i) and (ii).

For example, assuming similar or identical magnetic elements 210, 211, an orientation angle 280 during implantation, as depicted in FIG. 2B, of approximately 180 degrees, and no significant orientation differences along the second transverse extents:

the longitudinal implantation extent 400*a*=approx. (2× magnetic element longitudinal extent)+mechanical connector longitudinal extent; and the transverse implantation extent 400*b*=approx. (1× largest magnetic element transverse extent).

After implantation, assuming the compact configuration and arrangement depicted in FIG. 2D (i) and (ii) or an orientation angle 280 of approximately 0 degrees (FIG. 2C), and assuming no significant orientation differences along the second transverse extent 200*f*:

the longitudinal implanted extent 200*d*=approx. (1× magnetic element longitudinal extent)+(0.5× mechanical connector longitudinal extent); and the transverse implanted extent 200*e*=approx. (2× largest magnetic element transverse extent).

This represents a:

significant increase in the transverse implanted extent 200*e* of approx. (1× largest magnetic element transverse extent); and a significant decrease in the longitudinal implanted extent 200*d* of approx. (lx magnetic element longitudinal extent)+(0.5× mechanical connector longitudinal extent).

In summary, the mechanical connector 250 is configured and arranged to:

resiliently retain a first orientation 280 between the first magnetic element 210 and the second magnetic element 211 when deployed (disposed in human or animal tissue); and assume a second orientation (not depicted) between the first magnetic element 210 and the second magnetic element 211 during implantation.

Optionally the mechanical connector 250 may be configured and arranged to assume a further orientation (not depicted) between the first magnetic element 210 and the second magnetic element 211 before implantation. Additionally or alternatively, this may be, wholly or partially, the second orientation (not depicted) before implantation.

The mechanical connector 250 provides a rigid connection between the first 210 and second 211 magnetic elements, constraining them in a predetermined and/or controlled configuration and arrangement. In general, the combination of magnetic elements 210, 211 so constrained may be predetermined and/or controlled to provide specific magnetic configurations and arrangements: before implantation (FIG. 2A), during implantation (FIG. 2B), after implantation (FIG. 2C, FIG. 2D), or any combination thereof.

The possible configurations and arrangements may be optimized to provide one or more desired outcomes. For example:
  if configuration and arrangement after implantation (FIG. 2C, 2D) is considered most important, a less optimal configuration and arrangement may be acceptable before and/or during implantation (FIG. 2B);
  if configuration and arrangement during implantation (FIG. 2B) is considered most important, a less optimal configuration and arrangement may be acceptable before (FIG. 2A) and/or after implantation (FIG. 2C, 2D);
  if insertion of the magnetic marker 200 into the implantation channel 400 is to be eased, the differences may be reduced between the magnetic marker volume before implantation (FIG. 2A) and the implantation volume (FIG. 2B). In particular, differences in transverse extent may be reduced;
  if removal of the magnetic marker 200 from the implantation channel 400 is to be eased, the differences may be reduced between the implantation volume (FIG. 2B) and the magnetic marker implanted volume (FIG. 2C, FIG. 2D). In particular, differences in transverse extent may be reduced;
  if resistance against movement of the magnetic marker 200 during implantation is to be increased, the differences may be increased between the magnetic marker volume before implantation (FIG. 2A) and the implantation volume (FIG. 2B). In particular, differences in transverse extent may be increased. This may be advantageous in preventing unwanted deployment of the implantable magnetic marker 200 during implantation. Additionally or alternatively, resistance against movement during implantation may be increased by increasing the differences between the implantation volume (FIG. 2B) and the magnetic marker implanted volume (FIG. 2C, FIG. 2D). In particular, differences in transverse extent may be increased;
  Additionally or alternatively, if resistance against movement of the magnetic marker 200 during implantation is to be increased, the orientation difference between the first 210 and second 211 magnetic elements before implantation (FIG. 2A) with an increased resilience to retain the orientation. After insertion of the magnetic marker 200 into the implantation channel 400, the increased resilience may exert an increased force against an inner surface of the bore 400b.

In general, the combination of magnetic elements 210, 211 so constrained may be predetermined and/or controlled to provide specific magnetic configurations and arrangements: after implantation (FIG. 2C, FIG. 2D).

For example, a first 210 and second 211 magnetic element may be retained after implantation in close proximity such that both poles are in close proximity to their corresponding poles in the other element—this may increase the outward magnetic field, and hence may increase detectability of the magnetic marker 200. An example is depicted in FIG. 3C (which is further explained below) where the north (N) poles 240, 241 and south (S) poles 245, 246 are disposed along the longitudinal plane 270, 271 for each magnetic element 210, 211. The north (N) poles 240, 241 are retained in close proximity by the mechanical connector 250, and the south (S) poles 245, 246 are also retained in close proximity by the mechanical connector 250. For an acceptable deployment, the mechanical connector 250 is configured and arranged to overcome the repulsive magnetic forces as the same poles are brought into close proximity. Optionally, as depicted in FIG. 3C, they may be brought into contact.

For example, a first 210 and second 211 magnetic element may be retained after implantation in close proximity such that one pole is in close proximity to the opposite pole of the other element—this may also increase the outward magnetic field, and hence may increase detectability of the magnetic marker 200. An example is depicted in FIGS. 10B and 10C (which are further explained below) where the north poles 240, 241 and south poles 245, 246 are disposed along an approximately transverse plane (not depicted, but approximately perpendicular to the longitudinal plane 270, 271) for each magnetic element 210, 211. The north pole 240 of the second magnetic element 211 is retained in close proximity to the south pole 245 of the first magnetic element 210 by the mechanical connector 250. For an acceptable deployment, the mechanical connector 250 is configured and arranged to allow the attractive magnetic force to bring the elements together as the opposite poles are brought into close proximity. Optionally, as depicted in FIG. 10C, they may be brought into contact.

The mechanical connector 250 may comprise any suitable material for exerting the restraining force, such as a metal. The mechanical connector 250 may be attached to the magnetic elements 210, 211 using any suitable means, such as welding, laser welding, bonding and/or gluing. The attachment may be at one or more positions such as the end of the magnetic elements 210, 211 and/or along one of the sides. Additionally or alternatively, attachment may be to an outer surface of the magnetic elements 210, 211 and/or to a suitable aperture or recess.

For example, the mechanical connector 250 may comprise one or more material, selected from the group comprising: super elastic material, pseudo elastic material, shape-memory material, titanium, stainless steel, surgical stainless steel, cobalt-chrome, nickel-titanium alloy (nitinol), platinum, tungsten, silver, gold, tantalum, iridium, or an alloy thereof, or any combination thereof.

In the context of this current disclosure, a magnetic element 210, 211 may be essentially one or more permanent magnets (coated or uncoated), or an assembly comprising one or more permanent magnets—these may be used interchangeably in all the embodiments described in this disclosure.

For example, any suitable neodymium permanent magnet may be used, with a relatively high magnetic strength being preferred. However, in practice, practical problems may occur:

not all permanent magnet materials are sufficiently biocompatible. When the outer surface of the permanent magnet comes into contact with human or animal tissue, corrosion may occur and/or unwanted chemical or biological reactions. Biocompatibility of a magnet may be improved by improving the surface finishing and/or applying a coating such as parylene, gold, nickel, etc. This may increase the cost price of such a magnetic element, and there may be adhesion problems of the coating. Also, surface finishes or coatings are prone to (partial) failure which would still expose the human body to less biocompatible magnets.

Figure 7A:
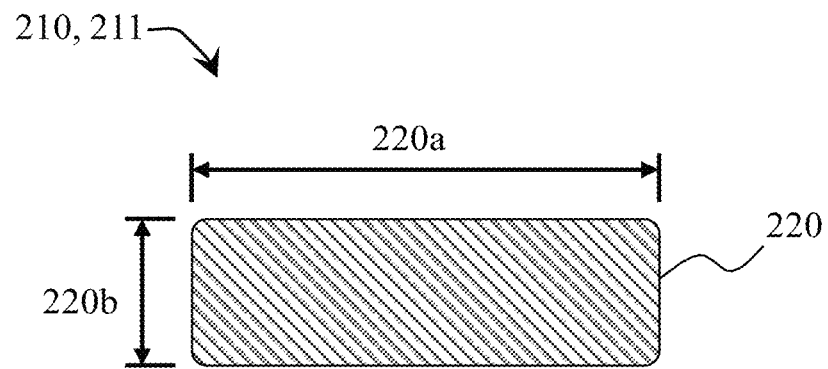
FIGS. 7A and 7B depict cross-sections through a permanent magnet and an optional enclosure for the permanent magnet.
Figure 7B:
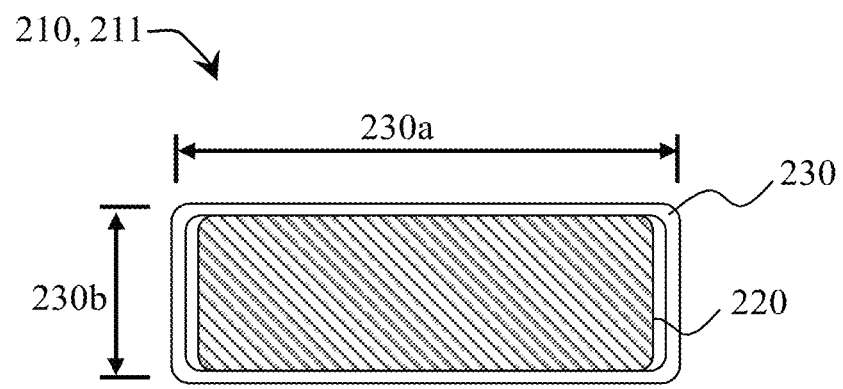

As depicted in FIG. 7B in longitudinal cross-section, the first 210 and/or second 211 magnetic element may alternatively comprise an enclosure 230 with a cavity, enclosing the permanent magnet 220 in said cavity. As it is the outer surfaces of the enclosure 230 which are exposed to tissue, the enclosure may be configured and arranged to comprise one or more materials with a higher degree of corrosion resistance and/or biocompatibility, such as titanium, stainless steel, surgical stainless steel, cobalt-chrome, nickel-titanium alloy (nitinol), platinum, tungsten, silver, gold, tantalum, iridium, or an alloy thereof, or any combination thereof.

In contrast, the permanent magnet 220 comprised in the cavity may be optimized for magnetic field strength without requiring such a high-degree of biocompatibility FIG. 7A depicts a longitudinal cross-section through a suitable permanent magnet 220. It has a magnetic element volume with a longitudinal extent 220a, a first transverse extent 220b and a second transverse extent (not depicted). This is comprised in the magnetic marker 200 volume. Depending on the number of magnetic elements, their configuration and their arrangement, it may determine one or more longitudinal extents or and/or one or more transverse extents of the magnetic marker 200.

In many embodiments, the largest of the first 220b and second transverse extents may determine the smallest transverse extent that an inner bore of an implantation channel should be to fully receive the magnetic marker 200. Typically, such a magnet 220 will have a longitudinal extent 220a as 4.7 mm. As it is being encapsulated, a negative tolerance is preferred, namely +0-0.10 mm. This example is cylindrical in shape, with a substantially round (circular) transverse cross-section with a transverse diameter 220b of 1.45 mm, with a negative tolerance of +0-0.10 mm. Optionally, a triangular, rectangular, polygonal, oval, elliptical transverse cross-section may also be used. Optionally, the edges may be rounded to avoid sharp edges—for example, at radius R0.10 mm. Although depicted as having a relatively constant longitudinal cross-section, other shapes may also be used, such as tapered, lozenge or bead shape.

FIG. 7B depicts a longitudinal cross-section through a suitable enclosed 230 permanent magnet 220. The enclosure 230 may also be described as a housing, a case, or a casing. In terms of this disclosure, an enclosure 230 is not a coating. It has a magnetic element volume with a longitudinal extent 230a, a first transverse extent 230b, and a second transverse extent (not depicted). This is comprised in the magnetic marker 200 volume. Depending on the number of magnetic elements with enclosures, their configuration and their arrangement, it may determine one or more longitudinal extents or and/or one or more transverse extents of the magnetic marker 200.

In many embodiments, the largest of the first 230b and second transverse extents may determine the smallest transverse extent that an inner bore of an implantation channel would need to be to fully receive the magnetic marker 200. Typically, such an encapsulated 230 magnet will have a longitudinal extent 230a as 5.2 mm+/−0.20 mm. This example is cylindrical in shape, with a substantially round (circular) transverse cross-section with a transverse diameter 230b of 1.65 mm+/−0.05 mm. Optionally, a triangular, rectangular, polygonal, oval, elliptical transverse cross-section may also be used. Optionally, the edges may be rounded to avoid sharp edges—for example, at radius R0.20 mm. Although depicted as having a relatively constant longitudinal cross-section, other shapes may also be used, such as tapered, lozenge or bead shape.

Additionally, the dimensions and shape of the enclosure 230 may be identical, similar, different to the corresponding dimensions and shapes of the enclosed magnet 220. This may be advantageous if permanent magnets are not available of the correct size and shape. Additionally or alternatively, more than one permanent magnet may be enclosed.

For example, a permanent magnet 220 with a longitudinal extent 220a of 1.45 mm and a first 220b and second (not depicted) transverse extent of 4.7 mm may be enclosed in an enclosure 230 with a wall thickness of 0.1 mm, to provide an assembled longitudinal extent 230a of 1.65 mm and an assembled first 230b and second (not depicted) transverse extent of 5.2 mm. Such a magnetic element assembly 210, 211 may be implanted using a 1.8 mm inner diameter (bore)/2.1 mm outer diameter 14G needle.

Optionally, the enclosure 230 is configured and arranged to substantially hermetically seal the permanent magnet 220 in said cavity. The degree to which the enclosure 230 should be sealed depends on the environmental conditions in the implant site and the degree of biocompatibility of the cavity, and in particular the biocompatibility of the permanent magnet 230.

Optionally, the enclosure 230 may comprise a plurality of enclosure parts, attached together to form outer walls of the enclosure 230, surrounding the permanent magnet 220 in said cavity. For example, the enclosure 230 may comprise a longitudinally-extended hollow sleeve, and two end caps. Alternatively or additionally, the enclosure 230 may comprise two longitudinally-extended hollow end caps. These parts may be made to mechanically fit together. However, other techniques such as welding, laser welding, bonding and/or gluing may also be used.

In the case that, an enclosure 230 is used to enclose one or more permanent magnets 220, the mechanical connector 250 may be attached to one or more suitable positions on the enclosure 230 and/or to one or more suitable positions on the permanent magnet. 220 Any suitable means, such as welding, laser welding, bonding and/or gluing, may be used. The attachment may be at one or more positions such as the end of the magnetic elements 210, 211 and/or along one of the sides. The attachment may be to an outer surface and/or to a suitable aperture or recess.

One or more attachments to the enclosure 230 may be advantageous when using permanent magnet materials to which attachment (for example, by gluing) may not be secure enough for reliable, regulated use, and welding is not feasible or desired. In addition, the risk of damage to the surface of the permanent magnet, which may create unwanted magnetized particles or debris, is reduced.

One or more attachments to the permanent magnet 220 may also be used with an enclosure 230—for example, through-holes may also be used, which allow attachment to the enclosure 230 and/or the permanent magnet 220 inside the cavity.

The mechanical connector 250 may be preformed to provide the predetermined orientation angle 280, it may be bent after implantation, it may be configured to bend after implantation, or some combination thereof.

Although depicted in two-dimensions, predetermining and/or controlling the orientation angle 280 and the degree of proximity may require optimization in more than one degree of freedom to achieve satisfactory deployment of the desired magnetic configuration and arrangement.

To simplify implantation, the mechanical connector 250 may be further configured and arranged to assume a second orientation angle 280 between the first longitudinal plane 270 and the second longitudinal plane 271, as depicted in FIGS. 2A and/or 2B, such that, before and/or during implantation, the largest transverse extent 200b is as small as possible. In most cases, this will increase the longitudinal extent 200a. In many cases, the longitudinal extent 200a is as large as possible.

This allows the magnetic marker 200 to be implanted using a hollow implantation channel 400, such as a needle. The largest transverse extent 200b of the magnetic marker 200, before and/or during implantation, is configured and arranged to fit into the bore 400b of the implantation channel 400. A suitable bore 400b may be an inner diameter slightly larger than the largest transverse extent 200b of the magnetic marker 200.

As permanent magnets are being implanted, it may be advantageous to use weakly magnetic materials in the implantation channel 400 with a reduced, a low or an insignificant degree of ferromagnetism when exposed to the field strengths produced by the permanent magnets used.

For example, a non-ferrous metal, titanium, aluminium, platinum, gold, silver, copper, a glass, PTFE, or a plastic. One of many steels may also be used, such as stainless steel, some martensitic stainless steels or one of many austenitic stainless steels. These materials exhibit a reduced, a low or an insignificant magnetic response, which may reduce or avoid the degree of magnetic attraction between the permanent magnets and the implantation channel 400.

Feebly magnetic compositions of such materials may be used. These have a relative permeability in the range $\mu r$=1.00001 to 2 or 1.00001 to 4, evaluated according to ASTM A342/A342M-14 (2014) Standard Test Methods for Permeability of Weakly Magnetic Materials.

After passing through the bore 400b, the implanted transverse extent 200ef of the magnetic marker 200 when retaining the first orientation angle 280 (after implantation as depicted in FIGS. 2C and 2D) is significantly greater than the transverse implantation extent 400b, which is less than or equal to the largest transverse extent of the bore 400b. In other words, the increase in implanted transverse extent 200ef after implantation means that when the mechanical connector 250 resiliently retains the first orientation angle 280, it is too extended to fit into the bore 400b of the implantation channel 400.

The second orientation angle 280 (not depicted in FIG. 2A or FIG. 2B) is preferably in the range 160 degrees to 200 degrees, and most preferably approximately 180 degrees.

For example, if the mechanical connector 250 comprises a spring steel, it may be configured and arranged to resiliently retain the implanted first orientation angle 280, depicted in FIG. 2C or 2D In the embodiments depicted in this disclosure, correct deployment requires predetermined and/or controlled dispositions of north and south magnetic poles. These may be predetermined by detecting the orientation before, during and/or after assembly and placing the poles in accordance with the predetermined dispositions.

Use of enclosure 230 allows the magnetic pole disposition to be configured and arranged to be the same, similar or different to the physical disposition of the magnetic element, allowing displacement and/or rotation.

It may be particularly advantageous to predetermine and/or control the disposition of the poles by configuring and arranging the permanent magnets 220 to rotate. When such a magnetic element is brought into close proximity to a different mechanical element, the rotatable permanent magnet 220 will rotate inside and independent of the enclosure to ensure that opposite poles face each other and therefore magnetic attraction will occur between the magnetic elements.

In such an embodiment, it may be advantageous to use weakly magnetic materials in the enclosure with a reduced, a low or an insignificant degree of ferromagnetism when exposed to the field strengths produced by the permanent magnets 220 used. For example, a non-ferrous metal, titanium, aluminium, platinum, gold, silver, copper, a glass, PTFE, or a plastic. One of many steels may also be used, such as stainless steel, some martensitic stainless steels or one of many austenitic stainless steels. These materials exhibit a reduced, a low or an insignificant magnetic response, which may reduce or avoid the degree of magnetic attraction between the permanent magnets and the enclosure 230.

Feebly magnetic compositions of such materials may be used. These have a relative permeability in the range $\mu r$=1.00001 to 2 or 1.00001 to 4, evaluated according to ASTM A342/A342M-14 (2014) Standard Test Methods for Permeability of Weakly Magnetic Materials.

Figure 2E:
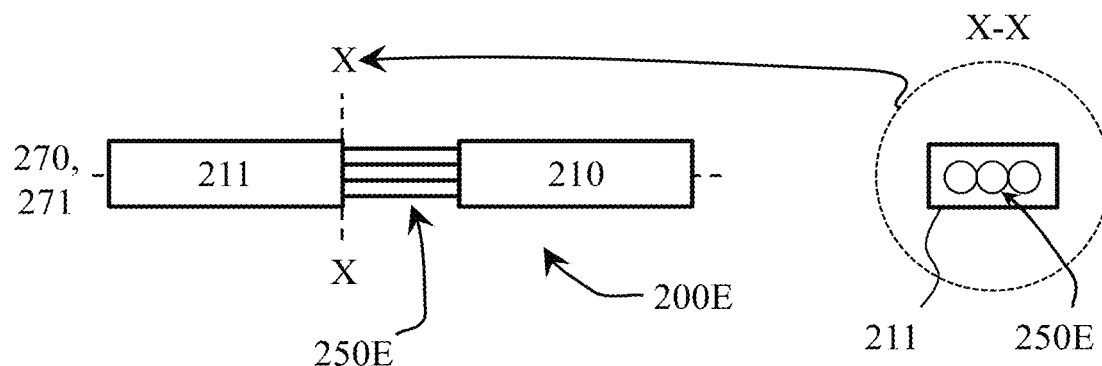
FIGS. 2E and 2F depict plan views and a transverse cross-section of modified first embodiments.
Figure 2F:
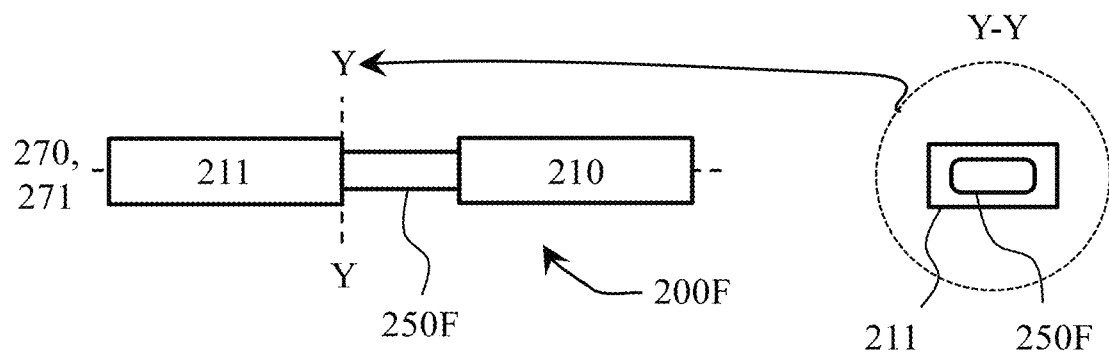
Figure 3A:
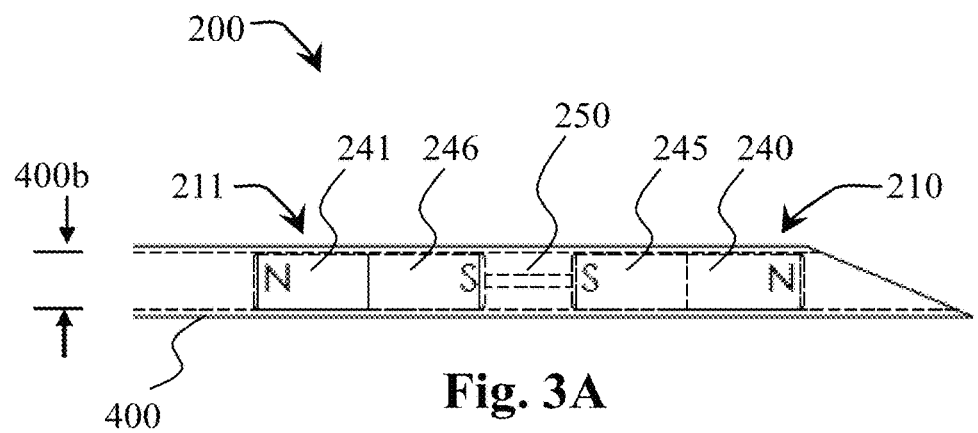
FIGS. 3A, 3B, and 3C depict schematically longitudinal cross-sections of how the magnetic marker depicted in FIG. 2 may be implanted.
Figure 3B:
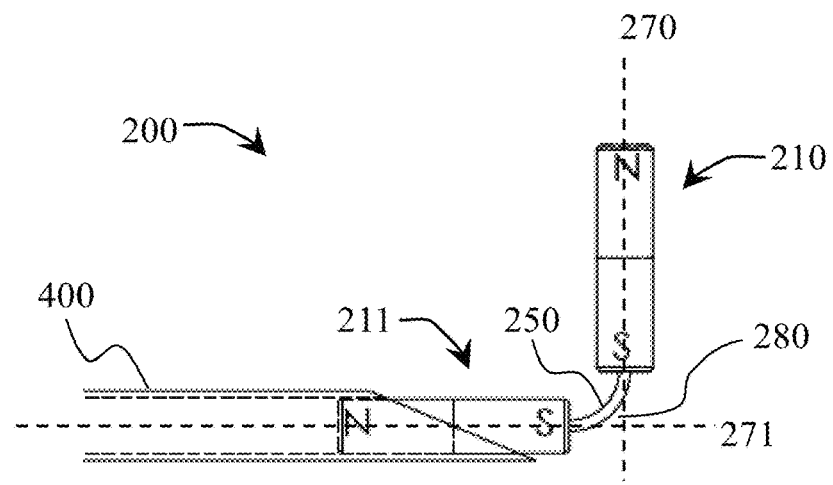
Figure 3C:
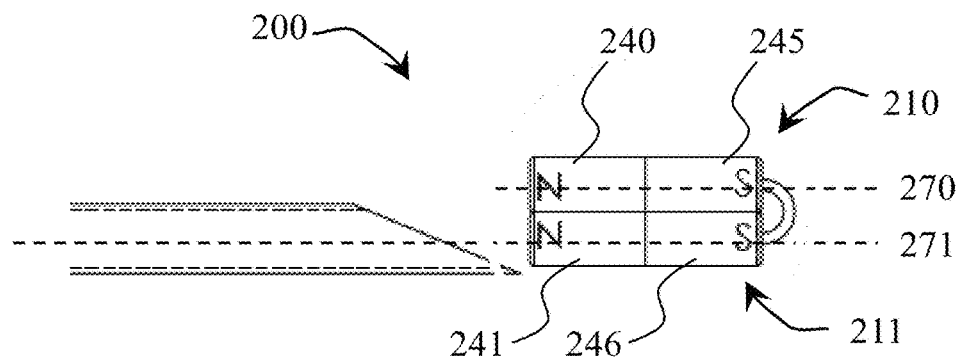

FIGS. 3A, 3B, and 3C depict schematically in longitudinal cross-section how the magnetic markers 200 depicted in FIG. 2 may be implanted. These figures depict possible static situations of a dynamic implantation process.

FIG. 3A depicts the same situation as depicted in FIG. 2B. The magnetic marker 200 is disposed in the inner bore 400b of an implantation channel 400, such as a hollow injection needle. The marker implantation volume is thus considered to have a longitudinal implantation extent equal to the longitudinal bore extent (not depicted), a first transverse extent equal to the first transverse bore extent 400b, and a second transverse extent equal to the second transverse bore extent (not depicted).

From left to right, FIG. 3A depicts magnetic elements 211 and 210, connected with a mechanical connector. The first magnetic element 210 is closest to the aperture of the implantation channel (depicted on the right-hand side), and will emerge first during implantation. Also depicted are the magnetic poles—from left to right (disposed along a longitudinal plane) north (N) 241 and south (S) 246 of the second magnetic element 211, and south (S) 245 and north (N) 240 of the first magnetic element 210. The mechanical connector 250 extends between the south (S) pole 246 of the second magnetic element 211 and the south (S) pole 245 of the first magnetic element 210. In other words, the magnetic maker 200 comprises:

[N 211 S]==[S 210 N]=>(aperture)

As depicted in 3A, the south (S) poles of the first 210 and second 211 magnetic elements are retained in close proximity by the mechanical connector 250. The mechanical connector 250 thus overcomes the repulsive magnetic forces to allow a predetermined and/or controlled configuration and/or arrangement before and/or during implantation.

A suitable bore 400b of the channel 400 may be an inner diameter slightly larger than the largest transverse extent (not depicted in FIG. 3A) of the magnetic marker 200. If the second orientation angle 280 (not depicted in FIG. 3A) is preferably in the range 160 degrees to 200 degrees, and most preferably approximately 180 degrees, the size of the bore 400b may be mainly determined using the largest transverse extent (or diameter) (not depicted) of the two or more magnetic elements 210, 211.

The volume of magnetic material to be implanted depends on parameters such as the first and second transverse extent (or diameter) of each magnetic element 210, 211, the length (or longitudinal extent) of each magnetic element 210, 211, the number of magnetic elements 210, 211 and the thickness of the optional enclosure 230 encapsulating one or more of the magnetic elements 210, 211.

The skilled person will realize that the extents of the magnetic elements 210, 211 and of the inner bore 400b of the channel 400 may be predetermined and/or controlled to provide a convenient implantation. For example, the dimensions and mechanical properties of injection needles are usually standardized, so it may be more convenient to select magnetic elements 210, 211 with extents that are suitable to pass through a standard inner bore 400b.

For example, the standards for stainless steel tubing for the manufacture of medical devices are found in ISO 9626, currently 9629:2016, published 2016-08: www.iso.org/standard/60480.html.

For example:

ID=Internal Diameter or bore of the injection channel 400 (mm)

OD=Outer Diameter (mm), WT=Wall Thickness (mm)

Volume=volume of magnetic material (mm$^3$) determined by the magnetic element dimensions (assuming cylindrical)=$L \cdot \pi \cdot D^2/4$ Max. Diam=maximum diameter to be implanted using a particular needle size. If the magnetic element is comprised in the optional enclosure 230 described above, then the diameter of the magnetic element to be implanted is reduced by the Wall Thickness of the enclosure 230 (e.g. 0.2 mm) (Max. Diam in enclosure 230)

The length of the magnetic element 210, 211 may be any suitable size. However, a length of 4.7 mm is assumed for the calculations below of magnetic material volume. If comprised in the optional enclosure 230, the total length of each housed element would be 5.2 mm.

| Needle size | ID | OD | WT | Max. Diam. | Max. Diam. in enclosure | Volume |
| --- | --- | --- | --- | --- | --- | --- |
| 14G | 1.7 | 2.1 | 0.2 | 1.65 | 1.45 | 7.76 |
| 16G | 1.3 | 1.6 | 0.15 | 1.25 | 1.05 | 4.07 |
| 18G | 1 | 1.2 | 0.1 | 1 | 0.8 | 2.36 |

The values for ID, OD and WT are approximations, used here just to explain the way in which magnetic volume may be estimated. The Max. Diam. was based upon these approximated OD's, using the same tolerances which appear suitable with a 14G needle (i.e. Max. Diam.=0.05 mm smaller than needle ID).

Max. Diam. in enclosure 230 was determined using the same enclosure 230 wall thickness (0.1 mm) and the ratio between enclosure 230 length and magnetic element length. For example, a titanium housing may be used with this wall thickness.

In the case (top row) that a single magnetic element 210, 211 with dimensions 1.45 mm×4.7 mm is implanted in an enclosure using a 14G needle, the magnetic material volume would be approx. 7.76 mm$^3$.

To implant a similar magnetic material volume using a 16G needle (middle row), at least two magnetic elements 210, 211 with dimensions of 1.05 mm×4.7 mm would be required.

To implant a similar magnetic material volume using a 18G needle (bottom row), at least four magnetic elements 210, 211 with dimensions of 0.8 mm×4.7 mm would be required.

For example, if the implantation channel 400 depicted in FIG. 3 is the bore 400b of a 16G needle, then the magnetic marker 200 comprising the first 210 and second 211 magnetic element connected by the mechanical connector 250 may represent a magnetic material volume of 8.14 mm$^3$.

Before and/or during implantation, a second orientation angle 280 is assumed between the first longitudinal plane 270 and the second longitudinal plane 271. This second orientation angle 280 is the orientation angle assumed for implantation—in this case, approximately 180 degrees, to allow a smaller diameter needles to be used.

Preferably, the mechanical connector 250 is configured and arranged to withstand the mechanical force exerted upon it in the needle bore 400b without undergoing plastic deformation.

The mechanical connector 250 may also be configured and arranged to resume (spring back to) a similar or identical shape (configuration and arrangement) to the "before implantation" after removal of the magnetic marker 200 from the bore 400b.

Particularly advantageous is configuring and arranging the mechanical connector 250 such that "before implantation" and "after implantation" are similar or identical. In this case, the magnetic marker 200 is temporarily unfolded (or extended) during implantation to pass through the implantation channel bore 400b.

FIG. 3B depicts the emergence of the first magnetic element 210 and the mechanical connector 250 from the aperture or the implantation channel 400 during implantation. In other words, "==[S 210 N]" emerges.

In this case, the mechanical connector 250 is configured and arranged to allow the orientation angle 280 between the first longitudinal plane 270 and the second longitudinal plane 271 to become approximately 90 degrees. In this case, this is an intermediate orientation angle between the implantation orientation (depicted in FIG. 3A) and the implanted orientation (depicted in FIG. 3C).

As depicted, the south (S) poles of the first 210 and second 211 magnetic elements are also retained in close proximity by the mechanical connector 250. The mechanical connector 250 thus overcomes the repulsive magnetic forces to allow a predetermined and/or controlled configuration and/or arrangement after implantation.

FIG. 3C depicts the completion of the implantation. In other words, "[N 211 S]" emerges.

The mechanical connector 250 allows the orientation angle (not depicted in FIG. 3C) between the first longitudinal plane 270 and the second longitudinal plane 271 to adopt its implanted orientation, and to retain it by applying a mechanical force. In this case, the first longitudinal plane 270 and the second longitudinal plane 271 are substantially parallel. This is substantially the same orientation as the orientation angle (not depicted in FIG. 3C) being approximately 0 degrees. The implanted configuration and arrangement is also depicted in FIGS. 2D(i) and 2D(ii).

As depicted, the south (S) poles 245, 246 of the magnetic elements 210, 211 are retained in very close proximity by the mechanical connector 250, and the north (N) poles 240, 241 of the magnetic elements are also retained in very close proximity by the mechanical connector 250. The mechanical connector 250 thus overcomes the repulsive magnetic forces to allow a predetermined and/or controlled configuration and/or arrangement. In other words, the implanted configuration and arrangement is schematically:

[N 210 S]=.
[N 211 S]='

Orientation angles close to 0 degrees or substantially parallel longitudinal planes 270, 271 are particularly advantageous as they provide implanted orientations with a reduced larger transverse extent. However, in practice, a larger orientation angle may be acceptable. For example, a higher degree of separation between the ends of the magnetic elements 210, 211 having the same pole may also be acceptable in practice. Such an embodiment may allow a mechanical connector 250 to be used that applies a relatively weaker mechanical force—for example, a thinner wire and/or ribbon may be used.

Using two magnetic elements 210, 211, with dimensions 1.05 mm×4.7 mm, comprising N52M magnetic material with a relative permeability of 1.05 and a permanent flux density of 1.46T directed along their longitudinal axes, simulations were performed to determine the effect of such a separation or non-zero orientation angle. The simulation values were compared with the simulated results for a single magnetic element with dimensions 1.45 mm×4.7 mm. The conclusions were that a separation of 2 mm or smaller, and that an orientation angle of between 0 and 50 degrees, did not significantly affect the magnetic field.

It may be particularly advantageous if the mechanical connector 250 comprises one or more super elastic material, pseudo elastic material, shape-memory material, nitinol, Fe—Mn—Si, Cu—Zn—Al and Cu—Al—Ni, or any combination thereof. These may be used to predetermine and/or control the configuration and arrangement of the magnetic elements.

This may allow an implantation orientation (e.g. in FIG. 3A) to be adopted temporarily and/or the implanted orientation (e.g. in FIG. 3C) to be adopted automatically.

Super elasticity, pseudo elasticity and shape-memory are physical characteristics of certain metallic alloys that allows these materials to be formed in a predetermined shape at high temperatures, after which they allow exceptional flexibility whilst still retaining their original shape (i.e. no or very limited plastic deformation).

For example, the mechanical connector 250 may be configured and arranged to be substantially straight (an orientation angle of approximately 180 degrees) when loaded within the bore 400 during implantation (FIG. 2A and FIG. 3A), and return substantially to a predetermined form when deployed (implanted—FIG. 3C) to constrain the magnetic elements 210, 211 in a predetermined and/or controlled magnetic configuration due to its super elastic properties.

Nitinol is a metal alloy of nickel and titanium, where the nickel and titanium are present in roughly equal atomic percentages. Different alloys are named according to the weight percentage of Nickel, such as Nitinol 55 and Nitinol 60. It exhibits the shape memory effect and super elasticity at different temperatures.

In the example depicted in FIG. 2A-2D, the mechanical connector 250 comprises a single nitinol wire with an approximately circular diameter in transverse cross-section.

For example, a diameter of 0.25 mm and a longitudinal extent (as depicted in the implantation orientation in FIG. 3A) of at least 1.96 mm may be used.

Mechanical connector 250 parameters that may be predetermined and/or controlled to configure and arrange the orientation angles 280 before, during and/or after implantation include:

- a longitudinal extent. It may be advantageous to use a longitudinal extent greater than 1.96 mm (1.96 mm represents the minimum longitudinal extent required to connect the two magnetic elements. 210, 211). In practice, increased longitudinal lengths, for example approx. 3 mm, may allow more flexibility in achieving the desired orientations, and in some case, may reduce the risk of plastic deformation;
- a transverse cross-section. Although depicted in FIG. 2A-2D with a substantially circular transverse cross-section wire, the mechanical connector 250 may have a circular, triangular, rectangular, square, polygonal, oval, elliptical cross-section or any combination thereof. The transverse cross-section may also vary at different points along its longitudinal extent;
- materials used. The materials used may also vary at different points along its longitudinal and/or transverse extent;
- a first and second transverse extent. The transverse extents may also vary at different points along its longitudinal extent;
- inclusion of one or more indentation, recess, groove, protrusion, ridge, cut, tapering, or similar at one or more positions along the longitudinal extent.
- inclusion in the interior of one or more voids, cavities, holes, channels or similar at one or more positions along the transverse extent. The mechanical connector 250 may optionally be substantially hollow. Such cavities may be at least partially filled by one or more similar or different materials.

Additionally or alternatively, a mechanical connector 250 may comprise one or more connector elements. For example, using two wires with identical, similar or different properties may also be used to configure and arrange the orientation angles 280 before, during and/or after implantation.

Additionally or alternatively, a mechanical connector 250 may comprise one or more connector elements either in close proximity or attached to each other.

FIG. 2E depicts an example of a modified 200E first embodiment of an implantable magnetic marker. It is the same as the magnetic marker 200 depicted in FIG. 2A-2D, except:

- as in FIG. 2A, a longitudinal cross-section is depicted through the magnetic marker. In this case, it is through the modified marker 200E comprising a modified mechanical connector 250E;
- the modified 200E first embodiment may have an identical, similar or different longitudinal extent. Additionally or alternatively, it may have an identical, similar or different first or second transverse extent;
- a dashed line X-X is indicated at the attachment point of the modified mechanical connector 250E to the second magnetic element 211. A transverse cross-section through this line X-X is also depicted;
- instead of a mechanical connector 250, comprising one wire with a substantially circular transverse cross-section, the modified mechanical connector 250E comprises a plurality of wires with substantially circular and similar transverse cross-sections.

in this example, three connector elements are rigidly attached to each other to form a ribbon-type of mechanical connector 250E, with a first transverse extent approximately equal to one diameter, and a second transverse extent approximately equal to three diameters.

The skilled person will realize that a plurality of connector elements may provide additional parameters to configure and arrange the orientation angles (not depicted in FIG. 2E) before, during and/or after implantation, such as:

using identical, similar or different properties, such as those described above, for one or more connector elements;

the proximity of the connector elements to each other;

the degree to which the connector elements are attached to each other. The attachment may also be varied at different positions along the longitudinal extent;

in the case that one or more transverse cross-sections are not substantially circular, the relative orientation of different faces of each connector element with respect to each other;

the relative transverse positions. For example, three connector elements may be arranged in a triangular configuration, four connector elements may be arranged in a square configuration, six connector elements may be arranged in a rectangular configuration. Additionally or alternatively, each row or column of connector elements (as viewed in transverse cross-section) may be offset by approximately half the diameter to provide a plurality of triangular configurations;

the orientation of the connector elements with respect to the one or more magnetic elements 210, 211. For example, bending is easier to occur where the transverse cross-section is smaller.

FIG. 2F depicts a further example of a modified 200F first embodiment of an implantable magnetic marker. It is the same as the magnetic marker 200 depicted in FIG. 2E, except:

as in FIG. 2E, a schematic plan view is depicted of the magnetic marker. In this case, it is through the modified marker 200F comprising a further modified mechanical connector 250F;

the modified 200F first embodiment may have an identical, similar or different longitudinal extent. Additionally or alternatively, it may have an identical, similar or different first or second transverse extent;

a dashed line Y-Y is indicated at the attachment point of the further modified mechanical connector 250FE to the second magnetic element 211. A transverse cross-section through this line Y-Y is also depicted;

instead of a mechanical connector 250E comprising three wires, a wire 250F with an approximately rectangular transverse cross-section is provided.

For example, the modified mechanical connector 250F may have transverse cross-sectional extents of 0.25 mm and 0.50 mm, and a longitudinal extent (as depicted in the orientation before and/or during implantation of FIG. 3A) of at least 1.96 mm. Alternatively, transverse cross-sectional extents of 0.2 mm×0.4 mm or 0.2 mm×0.6 mm may be advantageous. Alternatively or additionally, longitudinal extents of 3 mm or more may be advantageous.

It will be clear to the skilled person that the direction of bending may be influenced by predetermining and/or controlling the orientation of the smaller extent of the transverse cross-section. In other words, bending is easier through the smaller transverse cross-section (for example, in the 0.25 mm direction) than in the larger extent (for example, the 0.5 mm direction).

In general, the volume of magnetic material implanted may be increased by using a magnetic marker comprising additional magnetic elements, each one attached using an appropriately configured mechanical connector.

Figure 10A:
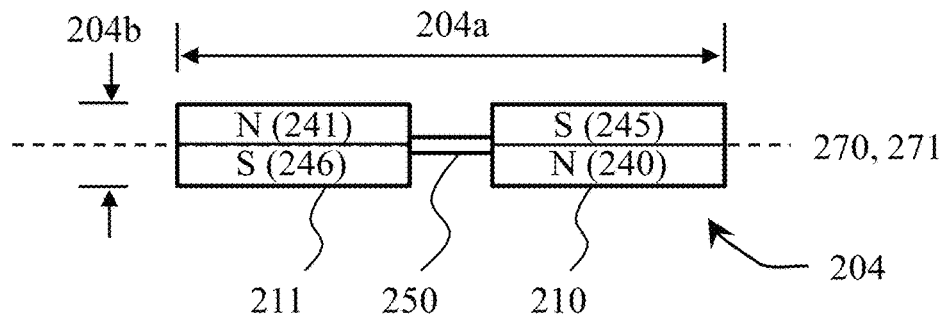
FIGS. 10A, 10B and 10C depict plan views of a further embodiment of an implantable magnetic marker.
Figure 10B:
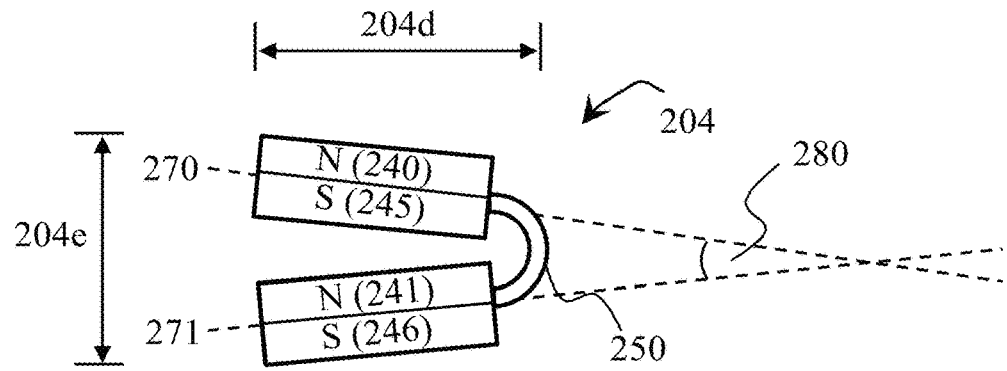
Figure 10C:
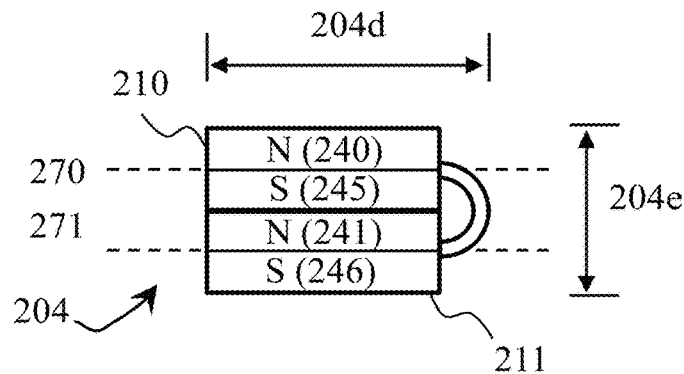

FIGS. 10A, 10B and 10C depict a further embodiment 204 of an implantable magnetic marker. FIG. 10A depicts a schematic plan view of the magnetic marker 204 before and/or during implantation. FIGS. 10B and 10C depict schematic plan views of the magnetic marker 204 after implantation. The marker 204 is the same as described above in relation to FIGS. 2A, 2B, 2C and 2D, and FIGS. 3A, 3B and 3C, except that:

as depicted in FIG. 10A, before and/or during implantation, the magnetic marker 204 has a marker volume with a longitudinal extent 204a, a first transverse extent 204b and a second transverse extent (not depicted). These extents 204a, 204b may be identical, similar or different compared to the respective extents 200a, 200b depicted in FIG. 2A;

as depicted in FIG. 10B, after implantation, the magnetic marker 204 has an implanted marker volume, with an implanted longitudinal extent 204d, a first transverse extent 204e and a second transverse extent (not depicted). These extents 204d, 204e may be identical, similar or different compared to the respective extents 200d, 200e depicted in FIG. 2C.

as depicted in FIG. 10C, after implantation, the magnetic marker 204 has an implanted marker volume, with an implanted longitudinal extent 204d, a first transverse extent 204e and a second transverse extent (not depicted). These extents 204d, 204e may be identical, similar or different compared to the respective extents 200d, 200e depicted in FIG. 2D.

for each magnetic element 210, 211, the north (N) poles 240, 241 and south (S) poles 245, 246 are disposed along an approximately a first transverse plane (not depicted, but approximately perpendicular to the longitudinal planes 270, 271), as depicted in FIG. 10A;

the mechanical connector 250 extends between:

a position between the north (N) pole 241 and south (S) pole 246 of the second magnetic element 211; and a position between the south (S) pole 245 and the north (N) pole 240 of the first magnetic element 210.

In other words, the magnetic maker 204 comprises:

[N] [S]

|211|====|210|

[S] [N]

As depicted in 10A, the south (S) pole 245 of the first magnetic element 210 and the north (N) pole 241 of the second magnetic element 211 are retained in close proximity by the mechanical connector 250. Additionally, the south (S) pole 246 of the second magnetic element 211 and the north (N) pole 240 of the first magnetic element 210 are retained in close proximity by the mechanical connector 250. The mechanical connector 250 thus overcomes the attractive magnetic forces to allow a predetermined and/or controlled configuration and/or arrangement before and/or during implantation.

The magnetic marker 204 may be implanted in a similar way to the embodiments described above in relation to FIGS. 2A, 2B, 2C and 2D, and FIGS. 3A, 3B and 3C, except that:

as depicted in FIGS. 10B and 10C, after implantation, the north (N) pole 241 of the second magnetic element 211 is retained in close proximity to the south (S) pole 245 of the first magnetic element 210 by the mechanical connector 250. In FIG. 10B, the first longitudinal plane 270 and the second longitudinal plane 271 intersect at an orientation angle 280 between 0 degrees and 50 degrees. Smaller orientation angles 280 may provide a more compact configuration of the magnetic elements 210, 211. Angles 280 close to 0 degrees may be considered substantially equivalent to the longitudinal planes 270, 271 being parallel as depicted in FIG. 10C.

The mechanical connector 250 is thus configured and arranged to allow the attractive magnetic forces to allow a predetermined and/or controlled configuration and/or arrangement wherein opposite poles of the magnetic elements are brought into close proximity (as in FIG. 10B), very close proximity or even into contact (as depicted in FIG. 10C).

In other words, the implanted configuration and arrangement is schematically:

[N]
|210|
[S]==.
[N]=='
|211|
[S]

For example, assuming similar or identical magnetic elements 210, 211, an orientation angle 280 during implantation, as depicted in FIG. 10A, of approximately 180 degrees, and no significant orientation differences along the second transverse extents:

the longitudinal implantation extent 204*a*=approx. (2× magnetic element longitudinal extent)+mechanical connector longitudinal extent; and the transverse implantation extent 204*b*=approx. (1× largest magnetic element transverse extent).

After implantation, assuming the compact configuration and arrangement depicted in FIG. 10C or an orientation angle 280 of approximately 0 degrees (FIG. 10B), and assuming no significant orientation differences along the second transverse extent (not depicted):

the longitudinal implanted extent 204*d*=approx. (1× magnetic element longitudinal extent)+(0.5× mechanical connector longitudinal extent); and the transverse implanted extent 204*e*=approx. (2× largest magnetic element transverse extent).

This represents a:

significant increase in the transverse implanted extent 204*e* of approx. (1x largest magnetic element transverse extent); and a significant decrease in the longitudinal implanted extent 204*d* of approx. (1x magnetic element longitudinal extent)+(0.5× mechanical connector longitudinal extent).

FIGS. 8A, 8B, 8C and 8D depict further embodiments 203, 206 of an implantable magnetic marker. FIG. 8A depicts a schematic plan view of the magnetic marker 203 before and/or during implantation. FIGS. 8B and 8C depict schematic plan views of the magnetic marker 203 after implantation. FIG. 8D depicts a schematic plan view of the magnetic marker 206 after implantation.

The marker 203 is the same as described above in relation to FIGS. 2A, 2B, 2C and 2D, and FIGS. 3A, 3B and 3C, except that:

as depicted in FIG. 8A, before and/or during implantation, the magnetic marker 203 has a marker volume with a longitudinal extent 203*a*, a first transverse extent 203*b* and a second transverse extent (not depicted). These extents 203*a*, 203*b* may be identical, similar or different compared to the respective extents 200*a*, 200*b* depicted in FIG. 2A;

as depicted in FIGS. 8B and 8C, after implantation, the magnetic marker 203 has an implanted marker volume, with an implanted longitudinal extent 203*d*, a first transverse extent 203*e* and a second transverse extent 203*f*. These extents 203*d*, 203*e*, 203*f* may be identical, similar or different compared to the respective extents 200*d*, 200*e*, 200*f* depicted in FIG. 2D(i) and (ii);

the mechanical marker 203 further comprises one or more mechanical anchors 260, 261, configured and arranged as one or more tissue anchors 260, 261, attached to the first magnetic element 210 at the end opposite to the mechanical connector 250.

extents 200*a*, 200*b* and the second transverse extent (not depicted) may also be determined by the shape of one or more mechanical anchors 260, 261, and the orientation between the one or more mechanical anchors (###) 260, 261 and the magnetic marker 203.

The magnetic maker 203 comprises:

[210]==[211]

In the same way as described above in relation to FIGS. 2A, 2B, 2C and 2D, and FIGS. 3A, 3B and 3C, the mechanical connector 250 may be configured and arranged:

to retain a first orientation (not depicted) when deployed; and to assume a second orientation (not depicted) during implantation;

to optionally assume a further orientation (not depicted) before implantation.

Magnetic marker 203 allows further configuration and arrangement: each mechanical anchor 260, 261 may be configured and arranged to resist changes in position of one or more magnetic elements 210, 211 when disposed in human or animal tissue. In other words, after deployment and/or after implantation, each mechanical anchor 260, 261 has a first anchor shape and/or a first anchor orientation to the magnetic marker 203, configured and arranged to provide significant resistance to changes in position of one or more magnetic elements 210, 211. Optionally, each tissue anchors 260, 261 may be arranged in one or more longitudinal and/or one or more transverse planes.

In general, tissue anchors, also called tissue fasteners or tissue fixings, are configured and arranged to resist movement of a magnetic element and/or the magnetic marker—for example, this may be used to assist fixation of the magnetic marker upon implantation and/or resist migration of the magnetic marker after implantation. Anchor is used as a generic term for any element that provides a degree of movement resistance due to physical parameters such as element 3D-shape, element dimensions, orientation to the magnetic marker, the presence of sharp points, the presence of hooks or barbs, surface profiles, surface roughness, protrusions, depressions, recesses, holes, or cavities. In some cases, resistance is provided directly after implantation, or it increases due to the promotion of tissue growth, or any combination thereof. Additional examples of mechanical anchors are depicted in FIGS. 13A-13I, and described below.

Additionally or alternatively, it may be advantageous to resist movement and/or migration due to magnetic attraction and/repulsion between:

proximate magnetic markers;
proximate magnetic elements;
a magnetic marker and any implantation channel;
a magnetic marker and any surgical instrument used before, during or after implantation;
or any combination thereof.

Additionally or alternatively, one or more mechanical anchors 260, 261 may be attached to:
- the second magnetic element 211 at the end opposite to the mechanical connector 250;
- the mechanical connector 250;
- the second magnetic element 211 at the end with the mechanical connector 250;
- the first magnetic element 210 at the end with the mechanical connector 250;
- and any combination thereof.

FIG. 8D depicts, after implantation, a modified implantable magnetic marker 206 with one tissue anchor 260 attached to the first magnetic element 210 at the end opposite to the mechanical connector 250 with an implanted longitudinal extent 206d. It may have a reduced first transverse extent 206e, after implantation, compared to the first transverse extent 203e of FIGS. 8B and 8C, if the largest transverse extent is determined by the tissue anchors 260, 261. In all other respects, the modified implantable marker 206, depicted in FIG. 8D, is the same as implantable marker 203, depicted in FIG. 8A-8C.

The one or more tissue anchors 260, 261 are configured and arranged using similar manufacturing and attachment techniques to the mechanical connector 250. In particular, the tissue anchors 260, 261 may comprise any suitable material for exerting the anchoring force, such as one or more metals and/or plastics. They may be blunt or pointed.

Similar to the mechanical connector 250, the one or more tissue anchors 260, 261 may comprise one or more: super elastic material, pseudo elastic material, shape-memory material, titanium, stainless steel, surgical stainless steel, cobalt-chrome, nickel-titanium alloy (nitinol), platinum, tungsten, silver, gold, tantalum, iridium, or an alloy thereof, or any combination thereof.

The tissue anchors 260, 261 may be attached to the magnetic elements 210, 211 using any suitable means, such as welding, laser welding, bonding and/or gluing. The attachment position may be at any suitable position, such as the end of the magnetic elements 210, 211 and/or along one of the sides.

Additionally or alternatively, the one or more tissue anchors 260, 261 may be integrated to a high degree with the one or more mechanical connectors 250.

If an enclosure 230 is used to enclose one or more magnetic elements 210, 211, the tissue anchors 260, 261 may be attached to one or more suitable positions on the enclosure 230 and/or to one or more suitable positions on the permanent magnet 220. The tissue anchors 260, 261 may be preformed to provide the predetermined anchor shape, it may be bent after implantation, it may be configured to bend after implantation, or some combination thereof.

For example, if a tissue anchor 260, 261 comprises a spring steel, it may be configured and arranged to retain the implanted shape and/or orientation, depicted in FIG. 8B, 8C or 8D. The tissue anchors 260, 261 may be further configured and arranged to allow a substantially flat and extended shape and/or orientation to be adopted before and/or during implantation, as depicted in FIG. 8A, whereby the magnetic marker 203, 206 may be inserted into the bore 400b of the implantation channel 400.

Alternatively, the tissue anchors 260, 261 may be configured and arranged to retain the substantially flat and extended shape, depicted in FIG. 8A. After implantation, a force or suitable delivery of energy may be applied to adopt the implanted shape and/or orientation depicted in FIG. 8B, 8C or 8D.

Figure 9A:
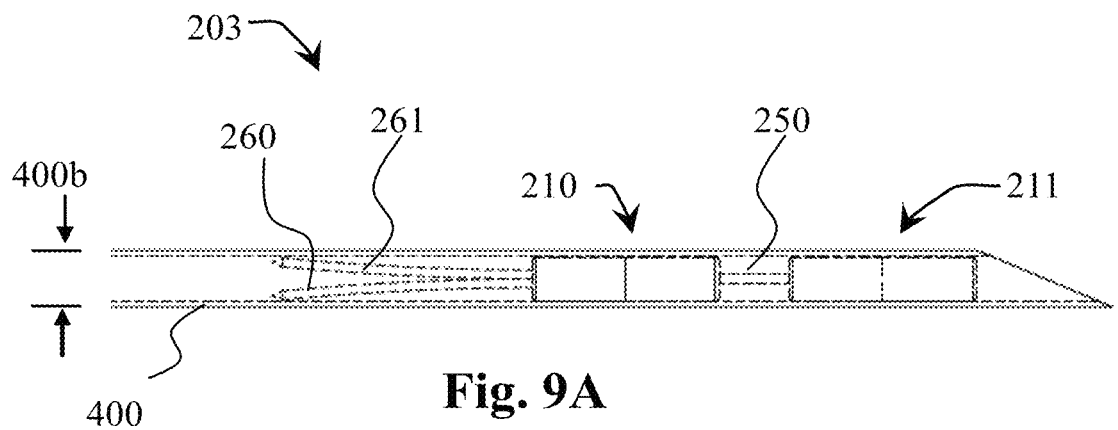
FIGS. 9A, 9B, and 9C depict schematically longitudinal cross-sections of how the magnetic marker depicted in FIG. 8 may be implanted.
Figure 9B:
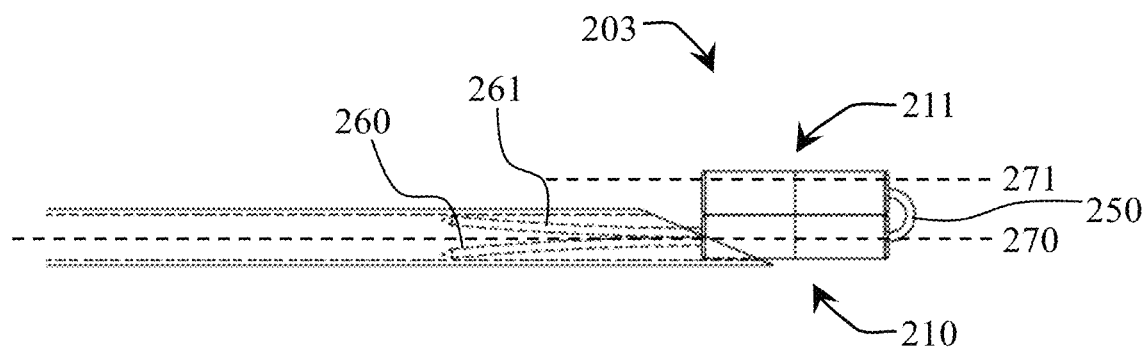
Figure 9C:
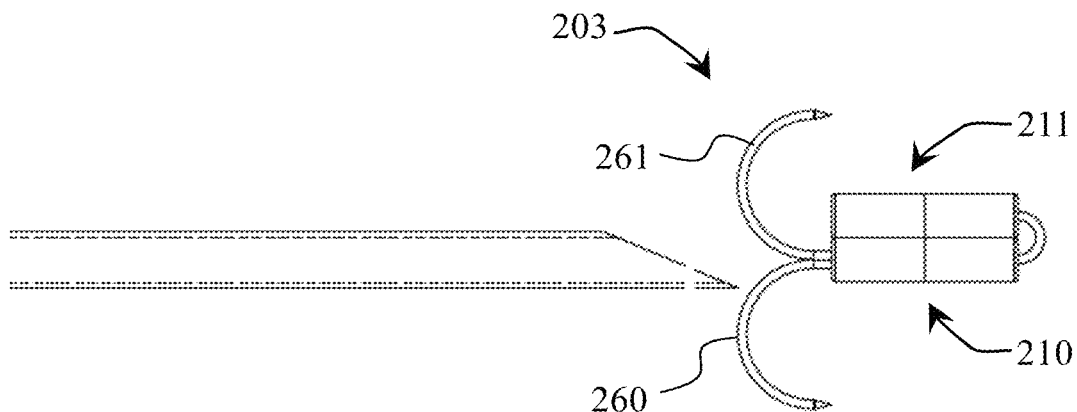

FIGS. 9A, 9B, and 9C depict schematically in longitudinal cross-section how the magnetic marker 203 depicted in FIG. 8 may be implanted. Implantation of the magnetic maker 206, depicted in FIG. 8D, may be implanted in an analogous way. These figures depict possible static situations of a dynamic implantation process.

As depicted in FIG. 9A, the magnetic marker 203 is disposed in the inner bore 400b of an implantation channel 400, such as a hollow injection needle. The marker implantation volume is thus considered to have a longitudinal implantation extent equal to the longitudinal bore extent (not depicted), a first transverse extent equal to the first transverse bore extent 400b, and a second transverse extent equal to the second transverse bore extent (not depicted).

From left to right, FIG. 9A depicts the first 260 and second 261 mechanical anchors (###), the first magnetic element 210, the mechanical connector 250 and the second magnetic element 211. The second magnetic element 211 is closest to the aperture of the implantation channel (depicted on the right-hand side), and will emerge first during implantation. The mechanical anchors 260, 261 are substantially flat and longitudinally extended (substantially retracted)

In other words, the magnetic maker 200 comprises:

[210]═[211]═>(aperture)

A suitable bore of the channel 400 may be an inner diameter slightly larger than the largest transverse extent (not depicted in FIG. 9) of the magnetic marker 203. If:
- the second orientation angle (not depicted in FIG. 9) is preferably in the range 160 degrees to 200 degrees, and most preferably approximately 180 degrees; and
- the transverse extent of the tissue anchors 260, 261 during implantation is less than or equal to the largest transverse extent of the magnetic elements 210, 211;

the size of the bore 400b may be mainly determined using the largest transverse extent (or diameter) (not depicted) of the two or more magnetic elements 210, 211.

FIG. 9B depicts the emergence of the first magnetic element, the mechanical connector 250 and the second magnetic element from the aperture of the implantation channel 400 during implantation. In other words,

[211]═.
[210]═' emerges.

In this case, the mechanical connector 250 is configured and arranged to allow the first longitudinal plane 270 and the second longitudinal plane 271 to become approximately parallel. This is equivalent to the orientation angle between the first longitudinal plane 270 and the second longitudinal plane 271 being approximately 0 degrees. In this case, this is the implanted orientation of the magnetic elements 210, 211 (as depicted in FIG. 8B). However, the mechanical anchors 260, 261 are not yet deployed.

FIG. 9C depicts the completion of the implantation, where the tissue anchors 260, 261 are deployed. In other words,

[211]═.
[210]═' emerges and is deployed.

After emerging from the aperture of the implantation channel 400, the mechanical anchors 260, 261 are allowed to adopt their first anchor shape and/or a first anchor orientation to the magnetic marker 203, as depicted in FIG. 8B. In this example, the first anchor shapes are approximately semicircular. Also in this example, the first anchor orientation is disposed in a transverse plane (transversely extended) through the first 210 and second 211 magnetic elements. Also, in this example, the largest transverse implanted extent 203e is determined by the perpendicular distance along the transverse plane between the outer edges of the first 260 and second 261 mechanical anchors.

For example, assuming similar or identical magnetic elements 210, 211, an orientation angle 280 during implantation, as depicted in FIG. 8A and FIG. 9A, of approximately 180 degrees, flat and extended mechanical anchors 260, 261, and no significant orientation differences along the second transverse extents:
- the longitudinal implantation extent 203a=approx. mechanical anchor longitudinal extent+(2× magnetic element longitudinal extent)+mechanical connector longitudinal extent; and the transverse implantation extent 203b=approx. (1× largest magnetic element transverse extent).

After implantation, assuming the compact magnetic element configuration and mechanical anchor arrangement depicted in FIG. 8B and FIG. 8C, and assuming no significant orientation differences along the second transverse extent (as depicted in FIG. 8C):
- the longitudinal implanted extent 203d=approx. (1× magnetic element longitudinal extent)+(0.5× mechanical connector longitudinal extent)+(0.5× mechanical anchor longitudinal extent); and the transverse implanted extent 203e=approx. (2×0.5× mechanical anchor longitudinal extent).

This represents a:
- significant increase in the transverse implanted extent 203e of approx. (1× mechanical anchor longitudinal extent)−(1× largest magnetic element transverse extent); and:
- a significant decrease in the longitudinal implanted extent 203d of approx. (0.5× mechanical anchor longitudinal extent)+(1× magnetic element longitudinal extent)+ (0.5× mechanical connector longitudinal extent).

It may be particularly advantageous if the one or more tissue anchors 260, 261 comprises one or more (super elastic material, pseudo elastic material, shape-memory material, nitinol, Fe—Mn—Si, Cu—Zn—Al and Cu—Al—Ni) or any combination thereof. This may allow an implantation (retracted) orientation (e.g. in FIG. 9A) to be adopted temporarily and/or the implanted (deployed) orientation (e.g. in FIG. 9C) to be adopted automatically.

Optionally, each mechanical anchor 260, 261 may be configured and arranged to:
- to assume a second anchor shape and/or second anchor orientation to the magnetic marker 203 (not depicted) during implantation; and/or
- to assume a further anchor shape and/or further anchor orientation to the magnetic marker 203 before implantation. Additionally or alternatively, this may be, wholly or partially, the second anchor shape and/or the second anchor orientation; and/or
- to exert a force against an inner surface of the bore 400b during implantation whereby the resistance against movement of the magnetic marker 203, 206 during implantation is significantly increased. This may be advantageous in preventing unwanted deployment of the implantable magnetic marker 203, 206 during implantation. For example, by configuring and arranging one or more mechanical anchors 260, 261 to be transversely extended during implantation.

Each mechanical anchor 260, 261 comprised in a magnetic marker 203 may be configured and arranged to provide identical, similar or different anchor shapes and/or anchor orientations. Each mechanical anchor 260, 261 may be oriented along the same or different longitudinal plane. Each mechanical anchor 260, 261 may be oriented along the same or different transverse plane.

FIG. 13A to 13I depict schematic plan views of number of further embodiments of an implantable magnetic marker 207A-I with one or more further examples of mechanical anchors 262A-I, configured and arranged as one or more tissue anchors 262A-I. Although depicted as a rectangle, each magnetic marker 207A-I may comprise one or more magnetic elements and one or more mechanical connectors—the mechanical anchors 262A-I may be rigidly attached to any element, connector or enclosure in any position or orientation, or any combination thereof. Each mechanical anchor 262A-I depicted, and any part thereof, may be employed separately or in combination.

Figure 13A:
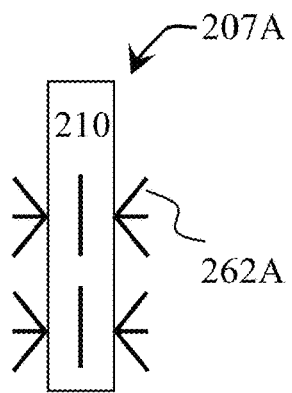
FIG. 13A to 13I depict schematic plan views of number of further embodiments of an implantable magnetic marker with one or more further examples of mechanical anchors.

The mechanical anchors are the same as those described above in relation to FIG. 8A-8D, except:

FIG. 13A depicts a magnetic marker 207A, comprising one or more bristles 262A disposed at one or more positions on the magnetic marker 207A. These bristles 262A may be regularly or irregularly spaced upon a portion of the magnetic marker 207A. Optionally, multiple bristles may be clustered together, as illustrated in FIG. 13A. Any type of bristle 262A may be used including, but not limited to, those that have a fractal-like fiber shape. The length, stiffness, and distribution of the bristle(s) 262A may be predetermined and/or controlled to provide a desired range of fixation.

Figure 13B:
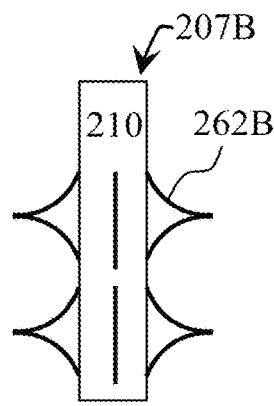

FIG. 13B depicts a magnetic marker 207B, comprising one or more expandable mechanical anchors 262B. In at least some embodiments, the magnetic marker 207B may implanted using an implantation channel (not depicted) having a suitable bore (or inner diameter). Before and/or during implantation, the magnetic marker 207B is inserted into the implantation channel, which surrounds the mechanical anchor 262B. During implantation, the mechanical anchors 262B are depressed transversely towards the magnetic marker 207B—in the case of a circular transverse cross-section, they may be depressed radially. When the implantation channel is removed, the mechanical anchors 262B expand into the nearby tissue. In at least one embodiment, the mechanical anchors 262B have a spring-like quality that results in the expansion of the mechanical anchors 262B when the implantation channel is removed. When more than one mechanical anchors 262B are provided, the more than one mechanical anchors 262B may be distributed in a regular or irregular pattern around the body of the magnetic marker 207B.

Figure 13C:
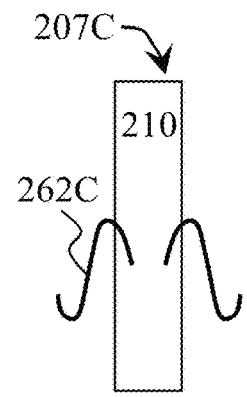

FIG. 13C depicts a magnetic marker 207C, comprising one or more mechanical barbs 262C that extend from one or more positions on the magnetic marker 207C. The mechanical barbs 262C may be hooked into surrounding tissue to provide a high degree of fixation. In some embodiments, the end of the mechanical barbs 262C may comprises one or more relatively rigid materials, and the rest of the mechanical barbs 262C may comprise one or more flexible materials. This may allow the mechanical barbs 262B to be depressed transversely towards the magnetic marker 207C for insertion into an implantation channel (not depicted)—in the case of a circular transverse cross-section, they may be depressed radially.

Figure 13D:
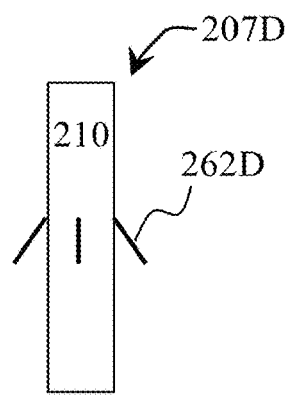

FIG. 13D depicts a magnetic marker 207D, comprising one or more mechanical tines 262D that extend from the magnetic marker 207D at an angle substantially less than 90 degrees. One or more mechanical tines 262D may be provided, distributed in any regular or irregular pattern including, but not limited to, one or more ring-like arrangements around the magnetic marker 207D.

Figure 13E:
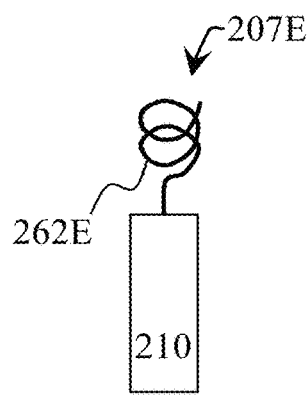

FIG. 13E depicts a magnetic marker 207E, comprising one or more mechanical pins 262E, rigidly attached at a longitudinal end of the magnetic marker 207E. The mechanical pin 262E may have any suitable shape, such a helical (as depicted), spiral, corkscrew or similar. In one embodiment, the mechanical pin 262E may be configured and arranged to be rotatable about a longitudinal axis during or after implantation to screw the mechanical pin 262E into tissue.

Figure 13F:
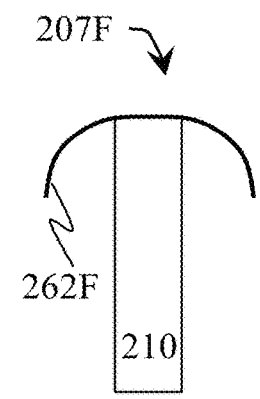

FIG. 13F depicts a magnetic marker 207F, comprising a shaped mechanical tip 262F at a longitudinal end of the magnetic marker 207F that permits a degree of tissue in-growth between one or more portions of the mechanical tip 262F or between the mechanical tip 262F and the magnetic marker 207F body. Preferably, the shaped mechanical tip 262F comprises material that is sufficiently flexible to be pushed through the bore of an implantation channel (not depicted), but also rigid enough to provide a high degree of fixation after tissue in-growth.

Figure 13G:
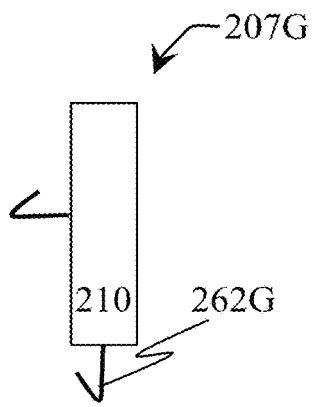

FIG. 13G depicts a magnetic marker 207G, comprising one or more mechanical hooks (or barbs) 262G that extend from one or more positions on the magnetic marker 207G. The mechanical hooks 262G may be hooked into surrounding tissue to provide a high degree of fixation. In some embodiments, the end of the mechanical hooks 262G may comprises one or more relatively rigid materials, and the rest of the mechanical hooks 262G may comprise one or more flexible materials. This may allow the mechanical barbs 262G to be depressed transversely towards the magnetic marker 207G for insertion into an implantation channel (not depicted)—in the case of a circular transverse cross-section, they may be depressed radially.

Figure 13H:
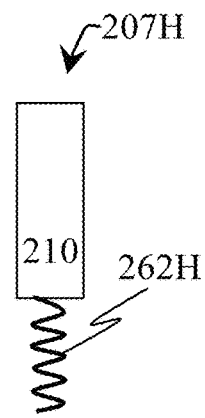
Figure 13I:
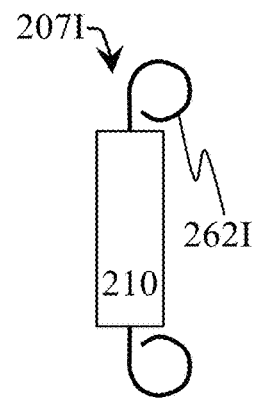

FIG. 13H depicts a magnetic marker 207H, comprising one or more mechanical springs 262H, rigidly attached at a longitudinal end of the magnetic marker 207H. The mechanical spring 262H may have any suitable shape, such a helical (as depicted), spiral, corkscrew, serpentine or similar. In one embodiment, the mechanical spring 262H may be configured and arranged to be rotatable about a longitudinal axis during or after implantation to screw the mechanical pin 262H into tissue FIG. 13I depicts a magnetic marker 207I, comprising one or more mechanical loops 262I at one or more longitudinal ends of the magnetic marker 207I that permit a degree of tissue in-growth within the one or more mechanical loop 262I. Preferably, the shaped mechanical loop 262I comprises material that is sufficiently flexible to be pushed through the bore of an implantation channel (not depicted), but also rigid enough to provide a high degree of fixation after tissue in-growth.

Figure 4A:
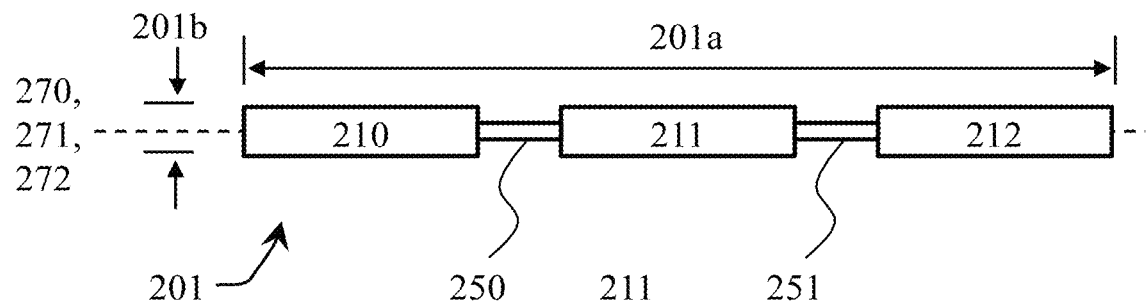
FIGS. 4A, 4B and 4C depict plan views of a further embodiment of an implantable magnetic marker.
Figure 4B:
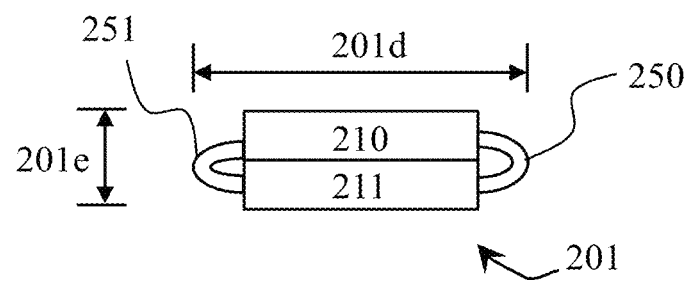
Figure 4C:
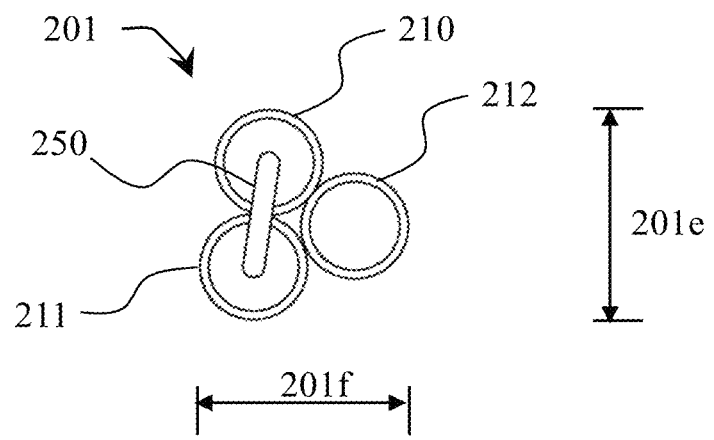

FIGS. 4A, 4B and 4C depict a further embodiment 201 of an implantable magnetic marker. FIG. 4A depicts a schematic plan view of the magnetic marker 201 before and/or during implantation. FIGS. 4B and 4C depict schematic plan views of the magnetic marker 201 after implantation. The marker 201 is the same as described above in relation to FIGS. 2A, 2B, 2C and 2D, except:

as depicted in FIG. 4A, before and/or during implantation, the magnetic marker 201 has a marker volume with a longitudinal extent 201a, a first transverse extent 201b and a second transverse extent (not depicted). These extents 201a, 201b may be identical, similar or different compared to the respective extents 200a, 200b depicted in FIG. 2A;

as depicted in FIG. 4B, after implantation, the magnetic marker 201 has an implanted marker volume, with an implanted longitudinal extent 201d, a first transverse extent 201e and a second transverse extent (not depicted). These extents 201d, 201e may be identical, similar or different compared to the respective extents 200d, 200e depicted in FIG. 2C(i);

as depicted in FIG. 4C, after implantation, the magnetic marker 201 has an implanted marker volume, with an implanted longitudinal extent (not depicted), a first transverse extent 201e and a second transverse extent 201f. These extents 201e, 201f may be identical, similar or different compared to the respective extents 200e, 200f depicted in FIG. 2C(ii);

additionally, the magnetic marker 201 comprises a further magnetic element 212, disposed along a further central longitudinal plane 272, and comprising a permanent magnet with a further north pole and a further south pole;

a further mechanical connector 251, extending between the further magnetic element 212 and the second magnetic element 211, the further mechanical connector 251 being configured and arranged to:

resiliently retain a further first orientation (not depicted) between the further longitudinal plane and the second longitudinal plane 271 when deployed (disposed in human or animal tissue); and assume a further second orientation (not depicted) between the further longitudinal plane and the second longitudinal plane 271 during implantation.

extents 201a, 201b and the second transverse extent (not depicted) may also be determined by the outer edges of the further magnetic element 212, the further mechanical connector 251 and the orientation between the further magnetic element 212 and the second magnetic element 211.

The magnetic maker 201 comprises:

[210]==[211]==[212]

In general, the further mechanical connector 251 may be configured and arranged to be substantially the same as the first mechanical connector 250, similar to the first mechanical connector 250 or substantially different to the first mechanical connector 250.

Generally, in magnetic marker embodiments comprising three or more magnetic elements 210, 211, 212, the mechanical connectors 250, 251 may be configured to allow the two outer magnetic elements 210, 212 to fold towards a central magnetic element 211 to reduce the implanted longitudinal extent of the marker.

In this embodiment 201, the largest transverse extent 201ef after implantation (as depicted in FIGS. 4B and 4C) is reduced by configuring the further mechanical connector 251 to dispose the further magnetic element 212 against both the first 210 and second 211 magnetic elements in a stacked arrangement. When viewed end-on along the longitudinal plane, as depicted in FIG. 4C, the magnetic elements 210, 211, 212 appear to be arranged in a triangular orientation with respect to each other.

A further reduction in the largest transverse extent 201ef may be possible by using magnetic elements with an interlocking transverse cross-section, such as triangular, square or polygonal.

In addition, as depicted, the longitudinal planes comprising the magnetic elements 210, 211, 212 may be substantially parallel—as described above, this is not essential, but substantially parallel or at a small orientation angle is preferred.

FIGS. 5A, 5B, 5C, 5D and 5E depict schematically how the magnetic marker 201 depicted in FIG. 4 may be implanted.

Figure 5A:
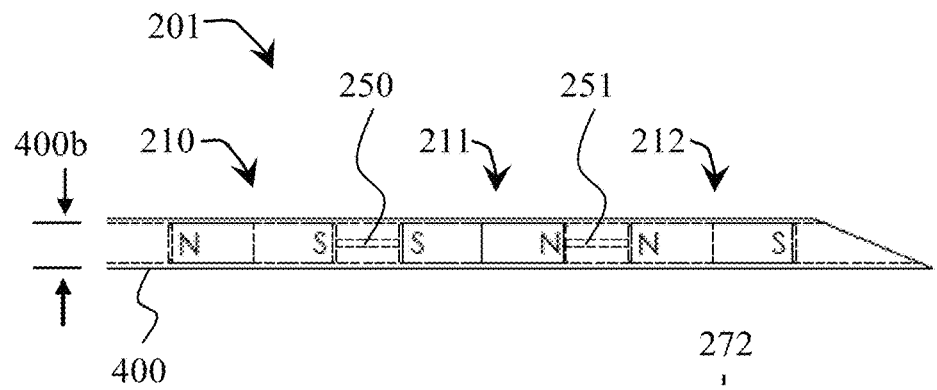
FIGS. 5A, 5B, 5C, 5D and 5E depict schematically longitudinal cross-sections of how the magnetic marker depicted in FIG. 4 may be implanted.

FIG. 5A depicts a longitudinal cross-section through the marker 201 disposed in the inner bore 400b of an implantation channel 400. The marker implantation volume is thus considered to have a longitudinal implantation extent equal to the longitudinal bore extent (not depicted), a first transverse extent equal to the first transverse bore extent 400b, and a second transverse extent equal to the second transverse bore extent (not depicted).

From left to right, FIG. 5A depicts the first magnetic element 210, the first mechanical connector 250, the second magnetic element 211, the further mechanical connector 251, and the further magnetic element 212. The further magnetic element 212 is closest to the aperture of the implantation channel (depicted on the right-hand side), and will emerge first during implantation.

Also depicted are the magnetic poles—from left to right (disposed along a longitudinal plane) north (N) and south (S) of the first magnetic element 210, south (S) and north (N) of the second magnetic element 211, and north (N) and south (S) of the further magnetic element 212. The further mechanical connector 251 extends between the north (N) pole of the second magnetic element 211 and the north (N) pole of the further magnetic element 212. The first mechanical connector 250 extends between the south (S) pole of the second magnetic element 211 and the south (S) pole of the first magnetic element 210.

In other words, the magnetic maker 201 comprises:
[N 210 S]==[S 211 N]==[N 212 S]=>(aperture)

As depicted in 5A, the north (N) poles of the further 212 and second 211 magnetic elements are retained in close proximity by the further mechanical connector 251, and the south (S) poles of the first 210 and second 211 magnetic elements are retained in close proximity by the first mechanical connector 250.

The mechanical connectors 250, 251 thus overcome the repulsive magnetic forces to allow a predetermined and/or controlled configuration and/or arrangement before and/or during implantation.

A suitable bore 400b of the channel 400 may be an inner diameter slightly larger than the largest transverse extent (not depicted in FIG. 5A) of the magnetic marker 201. If the second orientation angle 280 (not depicted in FIG. 5A) is preferably in the range 160 degrees to 200 degrees, and most preferably approximately 180 degrees, the size of the bore 400b may be mainly determined using the largest transverse extent (or diameter) (not depicted) of the three or more magnetic elements 210, 211, 212.

Figure 5B:
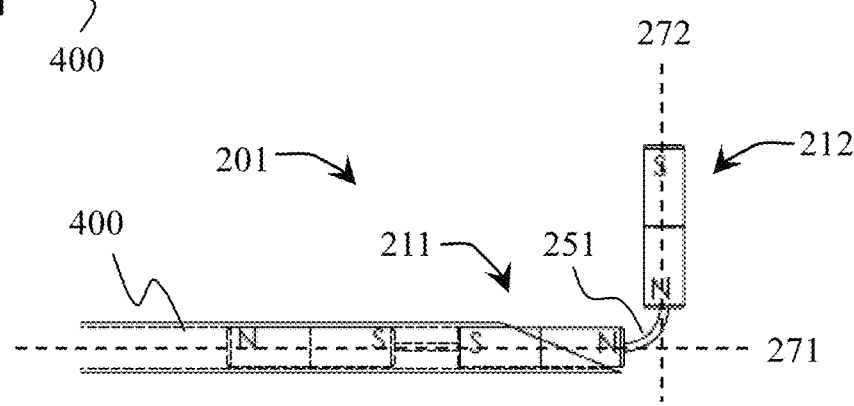

FIG. 5B depicts the emergence of the further magnetic element 212 and the further mechanical connector 251 from the aperture of the implantation channel 400 during implantation. In other words, "==[N 212 S]" emerges.

In this case, the further mechanical connector 251 is configured and arranged to allow the orientation angle (not depicted) between the further longitudinal plane 272 and the second longitudinal plane 271 to become approximately 90 degrees. In this case, this is an intermediate orientation angle between the implantation orientation (depicted in FIG. 5A) and the implanted orientation (depicted in FIG. 5E).

As depicted, the north (N) poles of the further 212 and second 211 magnetic elements are also retained in close proximity by the further mechanical connector 251. The further mechanical connector 251 thus overcomes the repulsive magnetic forces to allow a predetermined and/or controlled configuration and/or arrangement after implantation.

Figure 5C:
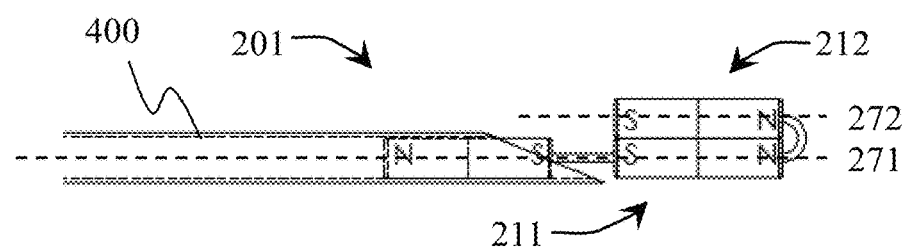
Figure 5D:
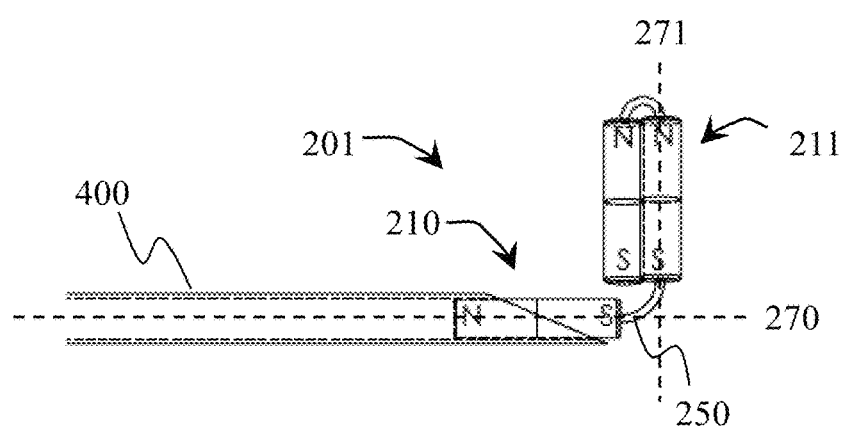

FIGS. 5C and 5D depict the emergence of the second magnetic element 211 from the implantation channel 400 during implantation. In other words, "==[S 211 N]==" emerges.

In this case, the mechanical connector 250 is configured and arranged to allow the orientation angle (not depicted) between the first longitudinal plane 270 and the second longitudinal plane 271 to become approximately 90 degrees (depicted in FIG. 5D). In this case, this is an intermediate orientation angle between the implantation orientation (depicted in FIG. 5A) and the implanted orientation (depicted in FIG. 4B, 4C, and FIG. 5E).

As depicted, the south (S) poles of the first 210 and second 211 magnetic elements are also retained in close proximity by the mechanical connector 250. The mechanical connector 250 thus overcomes the repulsive magnetic forces to allow a predetermined and/or controlled configuration and/or arrangement after implantation.

Figure 5E:
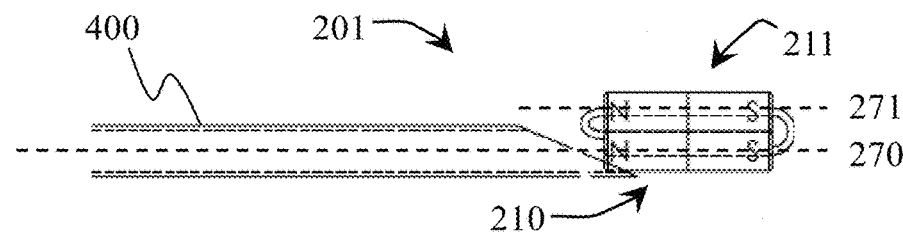

FIG. 5E depicts the completion of the implantation. In other words, "[N 210 S]==" emerges. The mechanical connector 250 allows the orientation angle between the first longitudinal plane 270 and the second longitudinal plane 271 to adopt its implanted orientation, and to retain it. In this case, the first longitudinal plane 270 and the second longitudinal plane 271 are substantially parallel. This is substantially the same orientation as the orientation angle (not depicted in FIG. 5E) being approximately 0 degrees. The implanted configuration and arrangement is also depicted in FIGS. 4B and 4C.

As depicted, the south (S) poles of the magnetic elements 210, 211 and 212 (not visible in FIG. 5E) are retained in very close proximity by the mechanical connectors 250, 251, and the north (N) poles of the magnetic elements are also retained in very close proximity by the mechanical connectors 250, 251. The mechanical connectors 250, 251 thus overcome the repulsive magnetic forces to allow a predetermined and/or controlled configuration and/or arrangement. In other words, the implanted configuration and arrangement is schematically:

.=[N 211 S]=.
'=[N 212 S]|
[N 210 S]='

For example, assuming similar or identical magnetic elements 210, 211, 212, orientation angles during implantation, as depicted in FIGS. 4A and 5A, of approximately 180 degrees, and no significant orientation differences along the second transverse extents:

the longitudinal implantation extent 201a=approx. (3× magnetic element longitudinal extent)+(2× mechanical connector longitudinal extent); and the transverse implantation extent 201b=approx. (1× largest magnetic element transverse extent).

After implantation, assuming the compact configuration and arrangement depicted in FIG. 4B, 4C and FIG. 5E or orientation angles of approximately 0 degrees, and assuming no significant orientation differences along the second transverse extent 201f:

the longitudinal implanted extent 201d=approx. (1× magnetic element longitudinal extent)+(2×0.5× mechanical connector longitudinal extent); and the transverse implanted extent 201ef=approx. (2× largest magnetic element transverse extent).

This represents a:
significant increase in the transverse implanted extent 201ef of approx. (1× largest magnetic element transverse extent); and a significant decrease in the longitudinal implanted extent 201d of approx. (2× magnetic element longitudinal extent)+(1× mechanical connector longitudinal extent).

Figure 11A:
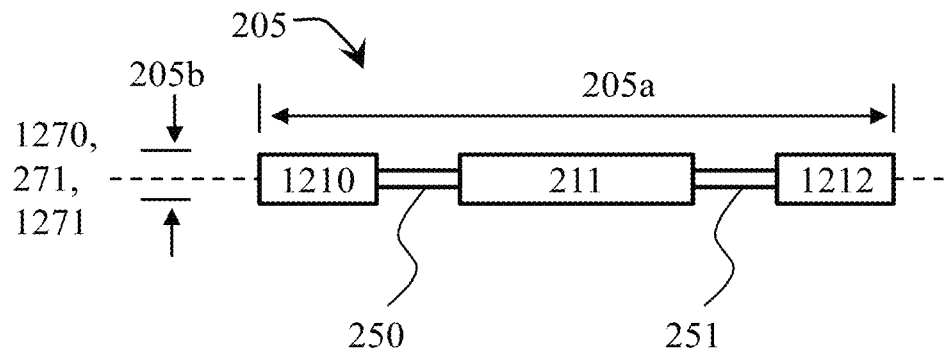
FIGS. 11A, 11B and 11C depict plan views of a further embodiment of an implantable magnetic marker.
Figure 11B:
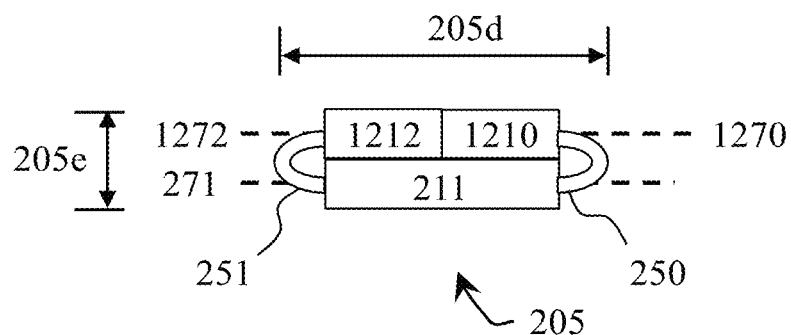
Figure 11C:
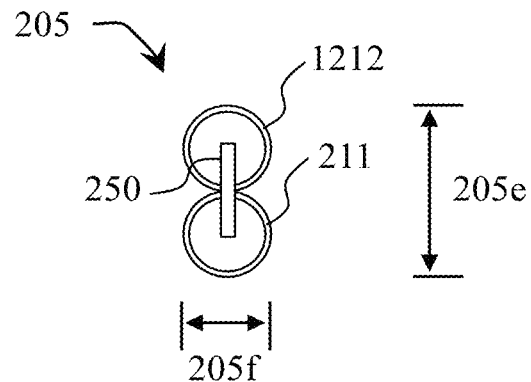

FIGS. 11A, 11B and 11C depict a further embodiment 205 of an implantable magnetic marker. FIG. 11A depicts a schematic plan view of the magnetic marker 205 before and/or during implantation. FIGS. 11B and 11C depict schematic plan views of the magnetic marker 205 after implantation. The marker 205 is the same as described above in relation to FIGS. 4A, 4B and 4C, except:

- as depicted in FIG. 11A, the magnetic marker 205 has a marker volume with a longitudinal extent 205a, a first transverse extent 205b and a second transverse extent (not depicted). These extents 205a, 205b may be identical, similar or different compared to the respective extents 201a, 201b depicted in FIG. 4A;
- as depicted in FIG. 11B, after implantation, the magnetic marker 205 has an implanted marker volume, with an implanted longitudinal extent 205d, a first transverse extent 205e and a second transverse extent (not depicted). These extents 205d, 205e may be identical, similar or different compared to the respective extents 201d, 201e depicted in FIG. 4B;
- as depicted in FIG. 11C, after implantation, the magnetic marker 205 has an implanted marker volume, with an implanted longitudinal extent (not depicted), a first transverse extent 205e and a second transverse extent 205f. These extents 205e, 205f may be identical, similar or different compared to the respective extents 201e, 201f depicted in FIG. 4C;
- in this embodiment, the first 1210 and further 1212 magnetic elements have a relatively smaller longitudinal extent. These longitudinal extents are substantially less (shorter) than the longitudinal extent of the central second magnetic element 211.

The magnetic maker 205 comprises:
[1210]==[211]==[1212]

As described for FIG. 4, the mechanical connectors 250, 251 may be configured to allow the two outer magnetic elements 1210, 1212 to fold towards a central second magnetic element 211 to reduce the implanted longitudinal extent 205d of the marker. However, by using shorter outer magnetic elements 1210, 1212, it may be possible to create a smaller increase in the largest transverse extent 205ef compared to the marker 201 of FIG. 4.

The smallest increase in the largest transverse extent 205ef may be provided if the further longitudinal plane 272 and the first longitudinal plane 270 substantially coincide, and the ends of the further magnetic element 1212 and the first magnetic element 1210 having opposite magnetic poles retained in proximity. For example, the longitudinal extent of the first 1210 and further 1212 magnetic elements may approximately half the longitudinal extent of the second magnetic element 211.

In addition, the use of the attraction due to the opposite poles of the reduced extent magnetic elements 1210, 1212 may reduce the risk of incorrect or insufficient deployment of the magnetic marker 205.

Figure 12A:
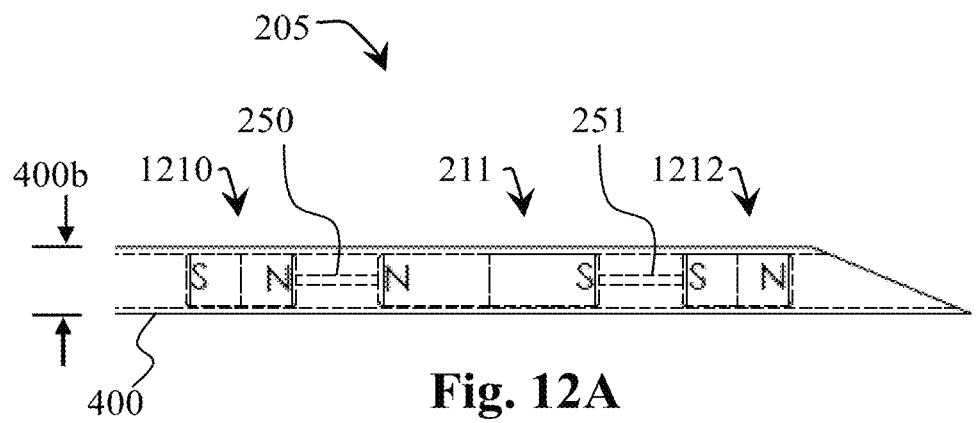
FIGS. 12A, 12B, and 12C depict schematically longitudinal cross-sections of how the magnetic marker depicted in FIG. 11 may be implanted.
Figure 12B:
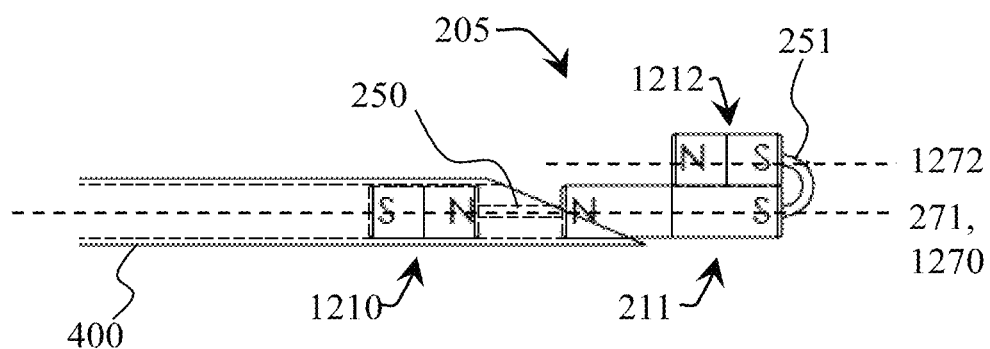
Figure 12C:
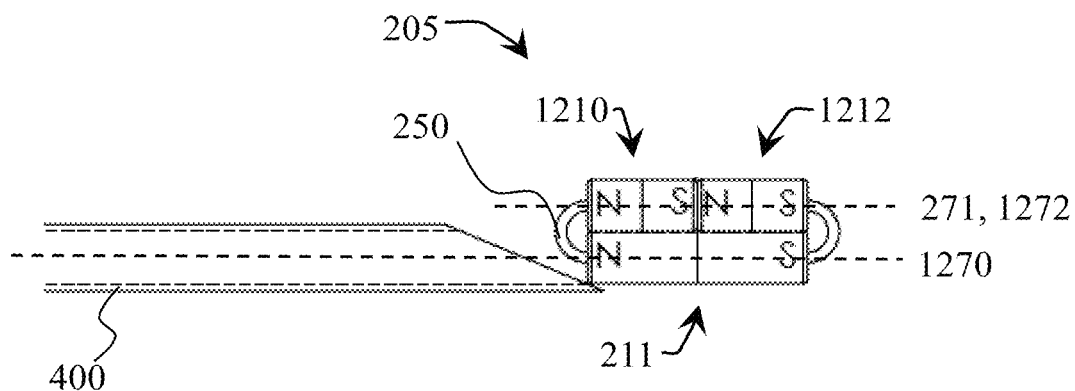

FIGS. 12A, 12B, and 12C depict schematically how the magnetic marker 205 depicted in FIG. 11 may be implanted.

FIG. 12A depicts a longitudinal cross-section through the marker 205 disposed in the inner bore 400b of an implantation channel 400. The marker implantation volume is thus considered to have a longitudinal implantation extent equal to the longitudinal bore extent (not depicted), a first transverse extent equal to the first transverse bore extent 400b, and a second transverse extent equal to the second transverse bore extent (not depicted).

From left to right, FIG. 12A depicts the shorter first magnetic element 1210, the first mechanical connector 250, the second magnetic element 211, the further mechanical connector 251, and the shorter further magnetic element 1212. The shorter further magnetic element 1212 is closest to the aperture of the implantation channel (depicted on the right-hand side), and will emerge first during implantation.

Also depicted are the magnetic poles—from left to right (disposed along a longitudinal plane) south (S) and north (N) of the shorter first magnetic element 1210, north (N) and south (S) of the second magnetic element 211, and south (S) and north (N) of the shorter further magnetic element 1212. The further mechanical connector 251 extends between the south (S) pole of the second magnetic element 211 and the south (S) pole of the shorter further magnetic element 1212. The first mechanical connector 250 extends between the north (N) pole of the second magnetic element 211 and the north (N) pole of the shorter first magnetic element 1210.

In other words, the magnetic maker 205 comprises:
[S 1210 N]==[N 211 S]==[S 1212 N]=>(aperture)

As depicted in 12A, the north (N) poles of the shorter first 1210 and second 211 magnetic elements are retained in close proximity by the first mechanical connector 250, and the south (S) poles of the shorter further 1212 and second 211 magnetic elements are retained in close proximity by the further mechanical connector 251.

A suitable bore 400b of the channel 400 may be an inner diameter slightly larger than the largest transverse extent (not depicted in FIG. 12A) of the magnetic marker 205. If the second orientation angles (not depicted in FIG. 12A) are preferably in the range 160 degrees to 200 degrees, and most preferably approximately 180 degrees, the size of the bore 400b may be mainly determined using the largest transverse extent (or diameter) (not depicted) of the three or more magnetic elements 1210, 211, 1212.

FIG. 12B depicts the emergence of the second magnetic element 211 and the further magnetic element 1212 from the aperture of the implantation channel 400 during implantation. In other words, "==[N 211 S]==[S 1212 N]" emerges.

In this case, the further mechanical connector 251 is configured and arranged to allow the orientation angle (not depicted) between the further longitudinal plane 1272 and the second longitudinal plane 271 to adopt its implanted orientation.

As depicted, the south (S) poles of the further 1212 and second 211 magnetic elements are also retained in close proximity by the further mechanical connector 251.

FIG. 12C depicts the completion of the implantation. In other words, "[S 1210 N]==" emerges.

The mechanical connector 250 allows the orientation angle between the first longitudinal plane 1270 and the second longitudinal plane 271 to adopt its implanted orientation, and to retain it. In this case, the first longitudinal plane 1270, the second longitudinal plane 271, and further longitudinal plane 1272 are substantially parallel. This is substantially the same orientation as the orientation angle (not depicted in FIG. 12C) being approximately 0 degrees. The implanted configuration and arrangement is also depicted in FIGS. 11B and 11C.

In addition, the further longitudinal plane 1272 and second longitudinal plane 271 substantially coincide, and the ends of the further magnetic element 1212 and the first magnetic element 1210 having opposite poles are retained in proximity.

As depicted, the south (S) poles of the magnetic elements 211 and 1212 are retained in very close proximity by the further mechanical connector 251, and the north (N) poles of the magnetic elements 1210 and 211 are retained in very close proximity by the first mechanical connectors 250.

In addition, the ends of the shorter further magnetic element 1212 and the shorter first magnetic element 1210 without mechanical connectors are retained in very close proximity by attractive force between the north (N) and the south (S) poles.

In other words, the implanted configuration and arrangement is schematically:

.=[S 1210 N] [S 1212 N]=.
'=[N 211 S]='

For example, assuming similar or identical shorter magnetic elements 1210, 1212, a second (longer) magnetic element 211 with similar transverse extent and twice the longitudinal extent, orientation angles during implantation (as depicted in FIGS. 11A and 12A) of approximately 180 degrees, and no significant orientation differences along the second transverse extents:

the longitudinal implantation extent 205*a*=approx. (1× longer magnetic element longitudinal extent)+(2×0.5× shorter magnetic element longitudinal extent)+(2× mechanical connector longitudinal extent); and the transverse implantation extent 205*b*=approx. (1× largest magnetic element transverse extent).

After implantation, assuming the compact configuration and arrangement depicted in FIG. 11B, 11C and FIG. 12C or orientation angles of approximately 0 degrees, and assuming no significant orientation differences along the second transverse extent 205*f*:

the longitudinal implanted extent 205*d*=approx. (2×0.5× shorter magnetic element longitudinal extent)+(2×0.5× mechanical connector longitudinal extent); and the transverse implanted extent 205*e*=approx. (2× largest magnetic element transverse extent).

This represents a:

significant increase in the transverse implanted extent 205*e* of approx. (1× largest magnetic element transverse extent); and a significant decrease in the longitudinal implanted extent 205*d* of approx. (1× longer magnetic element longitudinal extent)+(1× mechanical connector longitudinal extent).

Figure 6A:
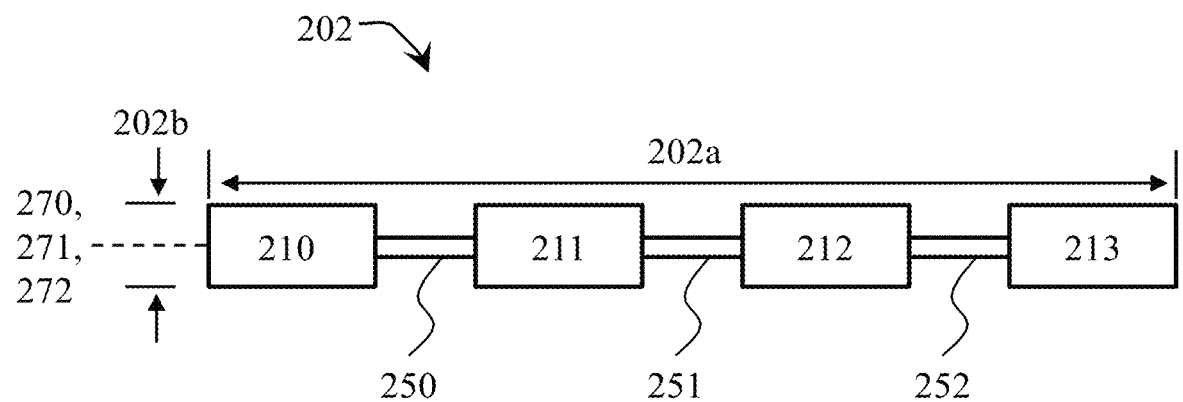
FIGS. 6A, 6B and 6C depict a plan views of a further embodiment of an implantable magnetic marker.
Figure 6B:
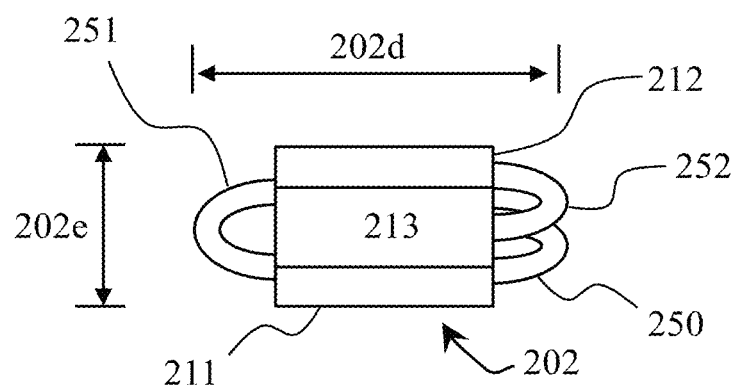
Figure 6C:
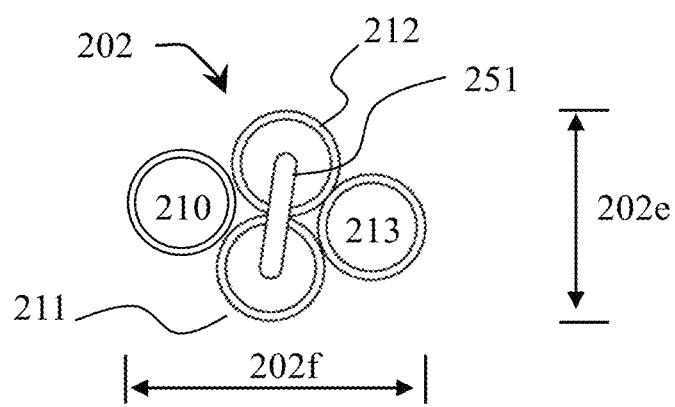

FIGS. 6A, 6B and 6C depict a further embodiment 202 of an implantable magnetic marker. FIG. 6A depicts a schematic plan view of the magnetic marker 202 before and/or during implantation. FIGS. 6B and 6C depict schematic plan views of the magnetic marker 202 after implantation. The marker 202 is the same as described above in relation to FIGS. 4A, 4B and 4C, except that it further comprises:—as depicted in FIG. 6A, the magnetic marker 202 has a marker volume with a longitudinal extent 202*a*, a first transverse extent 202*b* and a second transverse extent (not depicted). These extents 202*a*, 202*b* may be identical, similar or different compared to the respective extents 201*a*, 201*b* depicted in FIG. 4A;

as depicted in FIG. 6B, after implantation, the magnetic marker 202 has an implanted marker volume, with an implanted longitudinal extent 202*d*, a first transverse extent 202*e* and a second transverse extent (not depicted). These extents 202*d*, 202*e* may be identical, similar or different compared to the respective extents 201*d*, 201*e* depicted in FIG. 4B;

as depicted in FIG. 6C, after implantation, the magnetic marker 202 has an implanted marker volume, with an implanted longitudinal extent (not depicted), a first transverse extent 202*e* and a second transverse extent 202*f*. These extents 202*e*, 202*f* may be identical, similar or different compared to the respective extents 201*e*, 201*f* depicted in FIG. 4C;

the magnetic marker 202 also comprises an additional further 213 magnetic element disposing along an additional further longitudinal plane (not depicted), and comprising a permanent magnet with a further north pole and a further south pole;

an additional further mechanical connector 252, extending between the additional further 213 magnetic element and the further 212 magnetic element, the additional further mechanical connector 252 being configured and arranged to:

resiliently retain an additional further first orientation (not depicted) between the additional further longitudinal plane (not depicted) and the further longitudinal plane 272 when deployed; and assume an additional further second orientation (not depicted) between the additional further longitudinal plane (not depicted) and the further longitudinal plane 272 during implantation channel;

extents 202*a*, 202*b* and the second transverse extent (not depicted) may also be determined by the outer edges of the additional further magnetic element 213, the additional further mechanical connector 252 and the orientation between the further magnetic element 212 and the additional further magnetic element 213.

The magnetic maker 202 comprises:

[210]==[211]==[212]==[213]

In general, the additional further mechanical connector 252 may be configured and arranged to be substantially the same as the first mechanical connector 250, similar to the first mechanical connector 250 or substantially different to the first mechanical connector 250. Additionally or alternatively, the additional further mechanical connector 252 may be configured and arranged to be substantially the same as the further mechanical connector 251, similar to the further mechanical connector 251 or substantially different to the further mechanical connector 251.

Generally, in magnetic marker embodiments comprising four or more magnetic elements 210, 211, 212, 213, the mechanical connectors 250, 251, 252 may be configured to allow adjacent magnetic elements 210, 211, 212, 213 to fold towards each other to reduce the implanted longitudinal extent of the marker.

In this embodiment 202, the largest transverse extent 202*ef* after implantation (as depicted in FIGS. 6B and 6C) is reduced by configuring:

the additional further mechanical connector 252 to dispose the additional further magnetic element 213 against both the second 211 and further 212 magnetic elements in a stacked arrangement; and the first mechanical connector 250 to dispose the first magnetic element 210 against both the second 211 and further 212 magnetic elements on the opposite side in a further stacked arrangement.

When viewed end-on along the longitudinal plane, as depicted in FIG. 6C, the magnetic elements 210, 211, 212, 213 appear to be arranged in a diamond orientation with respect to each other.

A further reduction in the largest transverse extent 202*ef* may be possible by using magnetic elements with an interlocking transverse cross-section, such as triangular, square or polygonal.

In addition, as depicted, the longitudinal planes comprising the magnetic elements 210, 211, 212, 213 may be substantially parallel—as described above, this is not essential, but substantially parallel or at a small orientation angle is preferred.

Implantation may be performed in an analogous way to the magnetic marker 201, explained above in relation to FIG. 4 and FIG. 5.

For example, assuming similar or identical magnetic elements 210, 211, 212, 213, orientation angles during implantation, as depicted in FIG. 6A, of approximately 180 degrees, and no significant orientation differences along the second transverse extents:

the longitudinal implantation extent 202a=approx. (4× magnetic element longitudinal extent)+(3× mechanical connector longitudinal extent); and the transverse implantation extent 202b=approx. (1× largest magnetic element transverse extent).

After implantation, assuming the compact configuration and arrangement depicted in FIG. 6B and FIG. 6C or orientation angles of approximately 0 degrees, and assuming no significant orientation differences along the second transverse extent 202f:

the longitudinal implanted extent 202d=approx. (1× magnetic element longitudinal extent)+(2×0.5× mechanical connector longitudinal extent); and the transverse implanted extent 202f=approx. (3× largest magnetic element transverse extent).

This represents a:

significant increase in the transverse implanted extent 202f of approx. (2× largest magnetic element transverse extent); and a significant decrease in the longitudinal implanted extent 202d of approx. (3× magnetic element longitudinal extent)+(2× mechanical connector longitudinal extent).

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

For example:

one or more of the mechanical anchors 260, 261, 262A-I depicted in relation to FIG. 8, FIG. 9 and FIG. 13 may be comprised in any of the magnetic markers described herein;

any north (N) pole-south (S) pole polarities of the magnetic elements may be reversed;

the magnetic markers may be configured and arranged to be implanted in either direction—the first magnetic element to emerge from the implantation channel may be at either end;

the magnetic markers comprising one or more mechanical anchors may be configured and arranged to be implanted anchor-first and/or magnetic element first.

REFERENCE NUMBERS USED IN DRAWINGS

100 a magnetic marker field probe
110 one or more magnetic sensors
150 a probe longitudinal axis
160 a distal end of probe
200 a first embodiment of an implantable magnetic marker
200a a longitudinal extent of the first embodiment
200b a first transverse extent of the first embodiment
200d a longitudinal extent of the implanted first embodiment
200ef a transverse extent of the implanted first embodiment
200E-F modified first embodiments of an implantable magnetic marker
201 a second embodiment of an implantable magnetic marker
201a a longitudinal extent of the second embodiment
201b a first transverse extent of the second embodiment
201d a longitudinal extent of the implanted second embodiment
201ef a transverse extent of the implanted second embodiment
202 a third embodiment of an implantable magnetic marker
202a a longitudinal extent of the third embodiment
202b a first transverse extent of the third embodiment
202d a longitudinal extent of the implanted third embodiment
202ef a transverse extent of the implanted third embodiment
203 a fourth embodiment of an implantable magnetic marker
203a a longitudinal extent of the fourth embodiment
203b a first transverse extent of the fourth embodiment
203d a longitudinal extent of the implanted fourth embodiment
203ef a transverse extent of the implanted fourth embodiment
204 a fifth embodiment of an implantable magnetic marker
204a a longitudinal extent of the fifth embodiment
204b a first transverse extent of the fifth embodiment
204d a longitudinal extent of the implanted fifth embodiment
204e a first transverse extent of the implanted fifth embodiment
205 a sixth embodiment of an implantable magnetic marker
205a a longitudinal extent of the sixth embodiment
205b a first transverse extent of the sixth embodiment
205d a longitudinal extent of the implanted sixth embodiment
205ef a transverse extent of the implanted sixth embodiment
206 a seventh embodiment of an implantable magnetic marker
206d a longitudinal extent of the implanted seventh embodiment
206e a transverse extent of the implanted seventh embodiment
207A-I further embodiments of an implantable magnetic marker with one or more mechanical anchors
210 a first magnetic element
1210 a first magnetic element with a reduced longitudinal extent
211 a second magnetic element
212 a further magnetic element
1212 a further magnetic element with a reduced longitudinal extent
213 an additional further magnetic element
220 a permanent magnet
220a a longitudinal extent of the permanent magnet
220b a first transverse extent of the permanent magnet
230 an enclosure
230a a longitudinal extent of the enclosure
230b a first transverse extent of the enclosure
240 a first north pole
241 a second north pole
245 a first south pole
246 a second south pole
250 a first mechanical connector
250E-F modified first mechanical connectors
251 a further mechanical connector
252 an additional further mechanical connector
260 a first mechanical anchor configured as a first tissue anchor 261 a second mechanical anchor configured as a second tissue anchor
262A-I further mechanical anchors configured as further tissue anchors
270 a first central longitudinal plane for the first magnetic element
1270 a first central longitudinal plane for the first magnetic element with a reduced longitudinal extent
271 a second central longitudinal plane for the second magnetic element
272 a further central longitudinal plane for the further magnetic element
1272 a further central longitudinal plane for a further magnetic element with a reduced longitudinal extent
280 an orientation or an orientation angle
300 an outer surface of skin
400 an implantation channel, e.g. a hollow needle
400*a* a longitudinal bore extent
400*b* a first transverse bore extent

The invention claimed is:

1. An implantable magnetic marker for providing a detectable magnetic field, the marker comprising:
   a first magnetic element comprising a first permanent magnet with a north pole and a south pole;
   a second magnetic element comprising a second permanent magnet with a north pole and a south pole;
   a rigid bendable mechanical connector, extending between a rigid attachment to the first magnetic element and a rigid attachment to the second magnetic element, the mechanical connector being configured and arranged:
      to resiliently retain a first orientation between a first pole of the first permanent magnet and a first pole of the second permanent magnet when disposed in human or animal tissue, wherein the magnetic marker is bounded by an implanted marker volume with a longitudinal implanted extent and a transverse implanted extent; and
      to resiliently retain a second orientation between the first pole of the first permanent magnet and the first pole of the second permanent magnet during implantation, wherein the mechanical connector is longitudinally arranged between the first pole of the first permanent magnet and the first pole of the second permanent magnet and the magnetic marker is bounded by an implantation volume with a longitudinal implantation extent and a transverse implantation extent, whereby
      the transverse implanted extent is significantly greater than the transverse implantation extent and the longitudinal implanted extent is significantly less than longitudinal implantation extent;
   wherein the first pole of the first permanent magnet is the same pole as the first pole of the second permanent magnet, and the mechanical connector is configured and arranged to overcome a repulsive magnetic force between the first pole of the first permanent magnet and the first pole of the second permanent magnet.

2. The implantable magnetic marker according to claim 1, wherein the first and/or second magnetic elements comprise:
   an enclosure with a cavity, enclosing the permanent magnet in said cavity.

3. The implantable magnetic marker according to claim 2, wherein the one or more enclosures are configured and arranged to substantially hermetically seal the permanent magnet in said cavity.

4. The implantable magnetic marker according to claim 2, wherein the one or more enclosures are configured and arranged to allow the disposition of the north pole and/or south pole of the permanent magnet in said cavity to change during use.

5. The implantable magnetic marker according to claim 2, wherein the one or more enclosures comprise a material selected from the group comprising:
   titanium, stainless steel, surgical stainless steel, cobalt-chrome, nickel-titanium alloy (nitinol), platinum, tungsten, silver, gold, tantalum, iridium, or an alloy thereof, or any combination thereof.

6. The implantable magnetic marker according to claim 2, wherein the one more enclosures comprise a material selected from the group comprising:
   a non-ferrous metal, titanium, aluminium, platinum, gold, silver, copper, a glass, PTFE, a plastic, a weakly magnetic stainless steel, a weakly magnetic martensitic stainless steel, a weakly magnetic austenitic stainless steel, or any combination thereof.

7. The implantable magnetic marker according to claim 2, wherein the mechanical connector is rigidly attached to an outer surface of the enclosure comprised in the first and/or second magnetic elements.

8. The implantable magnetic marker according to claim 1, wherein the mechanical connector is rigidly attached to an outer surface of the first and/or second permanent magnets.

9. The implantable magnetic marker according to claim 1, wherein the mechanical connector comprises one or more material, selected from the group comprising:
   super elastic material, pseudo elastic material, shape-memory material, titanium, stainless steel, surgical stainless steel, cobalt-chrome, nickel-titanium alloy (nitinol), platinum, tungsten, silver, gold, tantalum, iridium, or an alloy thereof, or any combination thereof.

10. The implantable magnetic marker according to claim 1, wherein:
   the mechanical connector, extends between ends of the first and second magnetic elements having a same pole.

11. The implantable magnetic marker according to claim 10, wherein the ends of the first and second magnetic elements having the same pole are retained at a predetermined and/or controlled close proximity.

12. The implantable magnetic marker according to claim 1, wherein the first magnetic element is disposed along a first central longitudinal plane and the second magnetic element is disposed along a second central longitudinal plane, wherein the first and second orientations are determined respectively by a first and second angle of intersection between the first central longitudinal and the second central longitudinal plane.

13. The implantable magnetic marker according to claim 12, wherein the first intersection angle is in the range 0 degrees to 50 degrees.

14. The implantable magnetic marker according to claim 12, wherein the second intersection angle is in the range 160 degrees to 200 degrees.

15. The implantable magnetic marker according to claim 1, wherein the implantable magnetic marker further comprises one or more mechanical anchors, configured and arranged to resist changes in position of one or more magnetic elements when disposed in human or animal tissue.

16. The implantable magnetic marker according to claim 15, wherein the one or more mechanical anchors comprises one or more:

super elastic material, pseudo elastic material, shape-memory material, titanium, stainless steel, surgical stainless steel, cobalt-chrome, nickel-titanium alloy (nitinol), platinum, tungsten, silver, gold, tantalum, iridium, or an alloy thereof, or any combination thereof.

17. The implantable magnetic marker according to claim 15, wherein the one or more mechanical anchors are configured and arranged to be substantially retracted before and/or during implantation, and to be transversely extended after implantation.

18. The implantable magnetic marker according to claim 1, wherein the implantable magnetic marker further comprises:
  a third magnetic element comprising a third permanent magnet with a north pole and a south pole;
  a second rigid bendable mechanical connector, extending between a rigid attachment to the third magnetic element and a rigid attachment to the second magnetic element, the second mechanical connector being configured and arranged:
  to resiliently retain a third orientation between a first pole of the third permanent magnet and a second pole of the second permanent magnet when disposed in human or animal tissue, wherein the magnetic marker is bounded by the implanted marker volume with the longitudinal implanted extent and the transverse implanted extent; and
  to resiliently retain a fourth orientation between the first pole of the third permanent magnet and the second pole of the second permanent magnet during implantation, wherein the mechanical connector is longitudinally arranged between the first pole of the third permanent magnet and the second pole of the second permanent magnet and the magnetic marker is bounded by the implantation volume with the longitudinal implantation extent and the transverse implantation extent;
  wherein the first pole of the third permanent magnet is the same pole as the second pole of the second permanent magnet, and the second mechanical connector is configured and arranged to overcome a repulsive magnetic force between the first pole of the third permanent magnet and the second pole of the second permanent magnet.

19. The implantable magnetic marker according to claim 18, wherein the first and third magnetic elements have a longitudinal extent substantially less than a longitudinal extent of the second magnetic element.

20. The implantable magnetic marker according to claim 18, wherein the magnetic marker is configured and arranged such that:
  ends of the third magnetic element and the first magnetic element having opposite poles are retained at a predetermined and/or controlled close proximity.

21. A kit of parts for locating a tissue area of interest comprising:
  one or more implantable markers according to claim 1 including one or more permanent magnets; and
  a magnetic marker field probe having one or more magnetic sensors, configured and arranged to measure a magnetic field generated by the one or more permanent magnets after being disposed in human or animal tissue.

22. A method for implanting an implantable magnetic marker, the magnetic marker comprising:
  a first magnetic element comprising a first permanent magnet with a north pole and a south pole;
  a second magnetic element comprising a second permanent magnet with a north pole and a south pole;
  a rigid bendable mechanical connector, extending between a rigid attachment to the first magnetic element and a rigid attachment to the second magnetic element,
  the method comprising:
  after implantation, resiliently retaining a first orientation between a first pole of the first permanent magnet and a first pole of the second permanent magnet when disposed in human or animal tissue, wherein the magnetic marker is bounded by an implanted marker volume with a longitudinal implanted extent and a transverse implanted extent; and
  during implantation, resiliently retaining a second orientation between the first pole of the first permanent magnet and the first pole of the second permanent magnet, wherein the mechanical connector is longitudinally arranged between the first pole of the first permanent magnet and the first pole of the second permanent magnet and the magnetic marker is bounded by an implantation volume with a longitudinal implantation extent and a transverse implantation extent, whereby
  the transverse implanted extent is significantly greater than the transverse implantation extent; and
  the longitudinal implanted extent is significantly less than longitudinal implantation extent;
  wherein the first pole of the first permanent magnet is the same pole as the first pole of the second permanent magnet, and the mechanical connector is configured and arranged to overcome a repulsive magnetic force between the first pole of the first permanent magnet and the first pole of the second permanent magnet.

23. The method according to claim 22, wherein the method further comprises:
  during implantation, moving the magnetic marker through an implantation channel, the implantation channel having a transverse bore dimension equal to or greater than the transverse implantation extent of the magnetic marker.

24. The method according to claim 22, wherein the method further comprises:
  during and/or after implantation, resiliently retaining the north pole of the first magnetic element and the north pole or south pole of the second magnetic element in proximity, in close proximity, in very close proximity, in contact, or any combination thereof.

25. The method according to claim 22, wherein the method further comprises:
  during and/or after implantation, resiliently retaining the south pole of the first magnetic element and the north pole or south pole of the second magnetic element in proximity, in close proximity, in very close proximity, in contact, or any combination thereof.

26. The method according to claim 22, wherein the method further comprises:
  during and/or after implantation, folding the first magnetic element towards the second magnetic element and/or folding the second magnetic element towards the first magnetic element, whereby the longitudinal implanted extent is reduced compared to the longitudinal implantation extent.

27. The method according to claim 22, wherein the method further comprises:
  during and/or after implantation, folding the first magnetic element towards the second magnetic element and/or folding the second magnetic element towards the first magnetic element, whereby the transverse implanted extent is increased compared to the transverse implantation extent.

28. The method according to claim 22, wherein the magnetic marker further comprises one or more mechanical anchors, the method further comprising:

during implantation, allowing the one or more mechanical anchors to adopt a shape and/or an orientation to the magnetic marker, whereby a force is exerted against an inner surface of the implantation channel to provide a significant degree of resistance against movement of the magnetic marker through the implantation channel.

29. The method according to claim 22, wherein the magnetic marker further comprises:

a further magnetic element comprising a further permanent magnet with a north pole and a south pole;

a further rigid bendable mechanical connector, extending between a rigid attachment to the further magnetic element and a rigid attachment to the second magnetic element, the further mechanical connector being configured and arranged:

to resiliently retain a further first orientation between a first pole of the further permanent magnet and a second pole of the second permanent magnet element when disposed in human or animal tissue; and to resiliently retain a further second orientation between the first pole of the further permanent magnet and the second pole of the second permanent magnet during implantation;

wherein the first pole of the third permanent magnet is the same pole as the second pole of the second permanent magnet, and the second mechanical connector is configured and arranged to overcome a repulsive magnetic force between the first pole of the third permanent magnet and the second pole of the second permanent magnet;

the method further comprising:

during and/or after implantation, folding the first magnetic element towards the second magnetic element and/or folding the second magnetic element towards the first magnetic element; and during and/or after implantation, folding the further magnetic element towards the second magnetic element and/or folding the second magnetic element towards the further magnetic element;

whereby the longitudinal implanted extent is reduced compared to the longitudinal implantation extent.

* * * * *